US009770554B2

(12) United States Patent
Dollar et al.

(10) Patent No.: US 9,770,554 B2
(45) Date of Patent: Sep. 26, 2017

(54) CARDIOPLEGIA APPARATUS AND METHOD

(75) Inventors: Michael L. Dollar, Garland, TX (US); Cristo Suresh Corera, McKinney, TX (US); Kenneth A. Jones, McKinney, TX (US)

(73) Assignee: Quest Medical, Inc., Allen, TX (US)

( * ) Notice: Subject to any disclaimer, the term of this patent is extended or adjusted under 35 U.S.C. 154(b) by 0 days.

(21) Appl. No.: 13/613,705

(22) Filed: Sep. 13, 2012

(65) Prior Publication Data
US 2013/0190717 A1 Jul. 25, 2013

Related U.S. Application Data

(60) Provisional application No. 61/534,110, filed on Sep. 13, 2011.

(51) Int. Cl.
*A61M 5/172* (2006.01)
*G09B 23/28* (2006.01)
*A61M 1/36* (2006.01)
*G06F 19/00* (2011.01)

(52) U.S. Cl.
CPC ............ *A61M 5/172* (2013.01); *A61M 1/369* (2013.01); *A61M 1/3664* (2013.01); *G09B 23/285* (2013.01); *A61M 2205/505* (2013.01); *G06F 19/3406* (2013.01)

(58) Field of Classification Search
CPC .. A61M 5/172; A61M 1/3653; A61M 1/3664; A61M 2205/505; G09B 23/285; G06F 19/3406
USPC .................. 604/503, 505, 507, 151; 434/262
See application file for complete search history.

(56) References Cited

U.S. PATENT DOCUMENTS

| 4,236,880 | A |   | 12/1980 | Archibald |
|-----------|---|---|---------|-----------|
| 4,416,280 | A |   | 11/1983 | Carpenter et al. |
| 4,416,283 | A | * | 11/1983 | Slocum ........................ 607/32 |
| 4,427,709 | A |   | 1/1984  | Guhl et al. |
| 4,464,172 | A |   | 8/1984  | Lichtenstein |
| 4,466,804 | A |   | 8/1984  | Hino |
| 4,479,761 | A |   | 10/1984 | Bilstad et al. |
| 4,529,397 | A |   | 7/1985  | Hennemuth et al. |
| 4,568,330 | A |   | 2/1986  | Kujawski et al. |
| 4,657,490 | A |   | 4/1987  | Abbott |
| 4,696,671 | A |   | 9/1987  | Epstein et al. |

(Continued)

FOREIGN PATENT DOCUMENTS

WO    PCT/US12/55120    1/2013

*Primary Examiner* — Quynh-Nhu H Vu
(74) *Attorney, Agent, or Firm* — GrayRobinson, P.A.

(57) ABSTRACT

A microplegia console for controlling the delivery of cardioplegia to a patient, comprising an integrated display/touch screen for displaying cardioplegia information and patient information and allowing inputting of parameters via the display/touch screen into the console for computer-controlled perfusion of cardioplegia into the patient. The invention further comprises a method for delivery of cardioplegia to a patient, including defining and selecting a protocol from a displayed list and sequencing a series of the protocols. The invention also comprises a method for cardioplegia delivery to achieve aortic valve closure. Additionally, the invention comprises a method for activating an icon whereby, upon a first selection of the icon, displaying an indicia indicating that the icon has been first selected; and upon a second selection of the icon, activating the icon.

34 Claims, 41 Drawing Sheets

(56) References Cited

U.S. PATENT DOCUMENTS

| | | | |
|---|---|---|---|
| 4,710,166 A | 12/1987 | Thompson et al. | |
| 4,821,761 A | 4/1989 | Aid et al. | |
| 5,000,664 A | 3/1991 | Lawless et al. | |
| 5,055,013 A | 10/1991 | Faeser | |
| 5,056,992 A | 10/1991 | Simons et al. | |
| 5,165,873 A | 11/1992 | Meijer | |
| 5,217,355 A | 6/1993 | Hyman et al. | |
| 5,302,093 A | 4/1994 | Owens et al. | |
| 5,318,414 A | 6/1994 | Lundback | |
| 5,336,053 A | 8/1994 | Wynkoop | |
| 5,395,320 A | 3/1995 | Padda et al. | |
| 5,415,528 A | 5/1995 | Ogden et al. | |
| 5,419,684 A | 5/1995 | Struble et al. | |
| 5,441,392 A | 8/1995 | Lundback | |
| 5,554,013 A | 9/1996 | Owens et al. | |
| 5,573,502 A * | 11/1996 | LeCocq et al. | 604/4.01 |
| D376,848 S | 12/1996 | Zeilig et al. | |
| 5,584,667 A | 12/1996 | Davis | |
| 5,593,290 A | 1/1997 | Greisch et al. | |
| 5,609,575 A | 3/1997 | Larson et al. | |
| 5,620,312 A | 4/1997 | Hyman et al. | |
| 5,628,619 A | 5/1997 | Wilson | |
| D380,260 S | 6/1997 | Hyman | |
| 5,637,093 A | 6/1997 | Hyman et al. | |
| 5,702,358 A * | 12/1997 | Witherspoon | A61M 1/3664 128/DIG. 3 |
| 5,766,155 A | 6/1998 | Hyman et al. | |
| 5,791,880 A | 8/1998 | Wilson | |
| 5,795,327 A | 8/1998 | Wilson et al. | |
| 5,803,712 A | 9/1998 | Davis et al. | |
| 5,853,386 A | 12/1998 | Davis et al. | |
| 5,904,668 A | 5/1999 | Hyman et al. | |
| 5,993,420 A | 11/1999 | Hyman et al. | |
| 6,110,153 A | 8/2000 | Davis et al. | |
| 6,146,109 A | 11/2000 | Davis et al. | |
| 6,312,227 B1 | 11/2001 | Davis | |
| 6,468,242 B1 | 10/2002 | Wilson et al. | |
| 6,497,680 B1 | 12/2002 | Holst et al. | |
| 6,558,347 B1 | 5/2003 | Jhuboo et al. | |
| 6,620,187 B2 | 9/2003 | Carson et al. | |
| 6,660,027 B2 | 12/2003 | Gruszecki et al. | |
| 6,682,499 B2 | 1/2004 | Lenker | |
| 6,692,518 B2 | 2/2004 | Carson | |
| 6,699,267 B2 | 3/2004 | Voorhees et al. | |
| 6,742,992 B2 | 6/2004 | Davis | |
| 6,818,012 B2 | 11/2004 | Ellingboe | |
| 6,942,636 B2 | 9/2005 | Holst et al. | |
| 7,360,999 B2 | 4/2008 | Nelson et al. | |
| 7,402,154 B2 | 7/2008 | Holst et al. | |
| 7,407,489 B2 | 8/2008 | Holst et al. | |
| 7,442,183 B2 | 10/2008 | Baudino et al. | |
| 7,462,170 B2 | 12/2008 | Fournie et al. | |
| 7,481,787 B2 | 1/2009 | Gable et al. | |
| 7,520,871 B2 | 4/2009 | Yap et al. | |
| 7,527,608 B2 | 5/2009 | Mason | |
| 7,556,611 B2 | 7/2009 | Kolenbrander et al. | |
| 7,608,059 B2 | 10/2009 | Harr et al. | |
| 7,704,221 B2 | 4/2010 | Mannlein et al. | |
| 7,753,881 B2 | 7/2010 | Fournie et al. | |
| 7,753,883 B2 | 7/2010 | Fournie et al. | |
| 7,794,423 B2 | 9/2010 | Gaines et al. | |
| 7,842,003 B2 | 11/2010 | Jones et al. | |
| 7,860,542 B2 | 12/2010 | Sterling et al. | |
| 7,860,543 B2 | 12/2010 | Sterling et al. | |
| 7,862,535 B2 | 1/2011 | Gaines et al. | |
| 7,907,985 B2 | 3/2011 | Gable et al. | |
| 7,927,313 B2 | 4/2011 | Stewart et al. | |
| 7,935,074 B2 | 5/2011 | Plahey et al. | |
| 7,998,109 B2 | 8/2011 | Gaines et al. | |
| 8,034,028 B2 | 10/2011 | Fournie et al. | |
| 8,105,269 B2 | 1/2012 | Zhou | |
| 8,137,083 B2 | 3/2012 | Zhou | |
| 8,142,653 B2 | 3/2012 | Beden et al. | |
| 8,192,401 B2 | 6/2012 | Morris et al. | |
| 8,197,770 B2 | 6/2012 | Gable et al. | |
| 2006/0167400 A1* | 7/2006 | Ellingboe et al. | 604/6.14 |
| 2007/0190636 A1* | 8/2007 | Hassanein et al. | 435/284.1 |
| 2009/0099498 A1* | 4/2009 | Demers et al. | 604/6.09 |
| 2009/0305214 A1* | 12/2009 | Pybus | G09B 23/285 434/268 |

* cited by examiner

System Environment of MCR CONSOLE

FIG. 7-2A

New Case Setup

| | |
|---|---|
| Warm Temperature | 37°C |
| Start in | Warm / Cold |
| Circ System | Circ Off / Circ On |
| Heat Mode | 42°C Max / 39°C Max |
| Cold Mode | Continuous / Conserve Ice |

◁ 2 of 8 ▷

Prime

FIG. 7-4

New Case Setup

Retro Pressure (mmHg)

| Source | External | System |
|---|---|---|
| Upper Limit | 80 | 120 |
| Lower Limit | 10 | 10 |
| Auto Target | 35 | 50 |

◁ 4 of 8 ▷

Prime

FIG. 7-3

New Case Setup

Ante Pressure (mmHg)

| Source | External | System |
|---|---|---|
| Upper Limit | 250 | 250 |
| Lower Limit | 10 | 10 |
| Auto Target | 80 | 350 |

◁ 3 of 8 ▷

Prime

FIG. 7-5

New Case Setup

Vein Graft Pressure (mmHg)

| | |
|---|---|
| Upper Limit | 150 |
| Lower Limit | 10 |
| Auto Target | 120 |

◁ 5 of 8 ▷

Prime

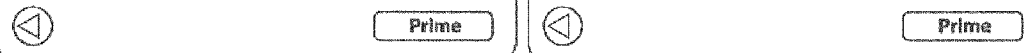
FIG. 7-6
FIG. 7-8
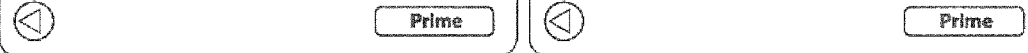
FIG. 7-7
FIG. 7-8A

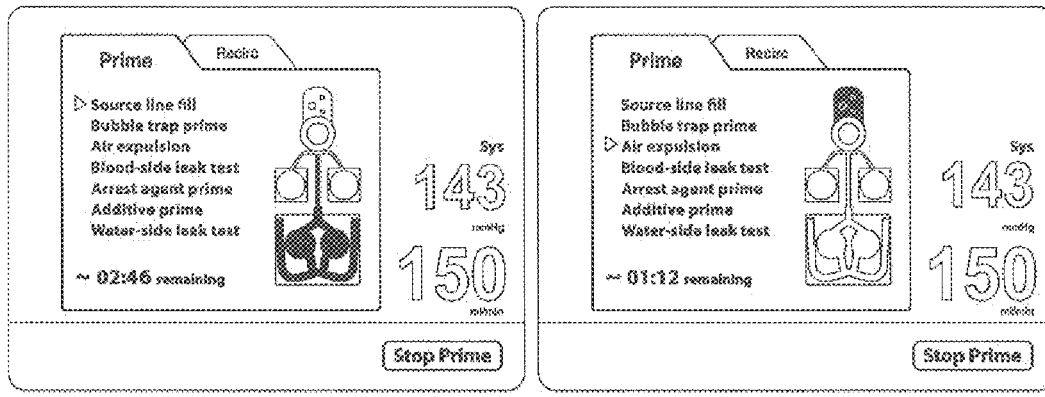
FIG. 8B
FIG. 8D
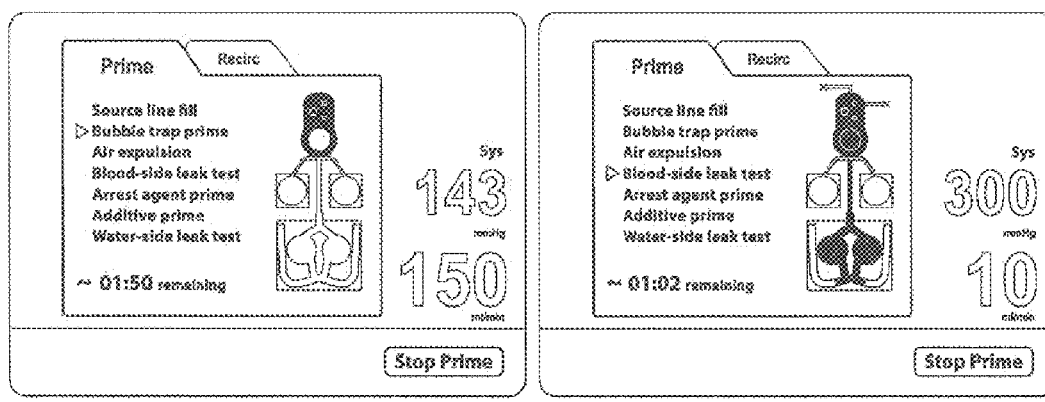
FIG. 8C
FIG. 8E

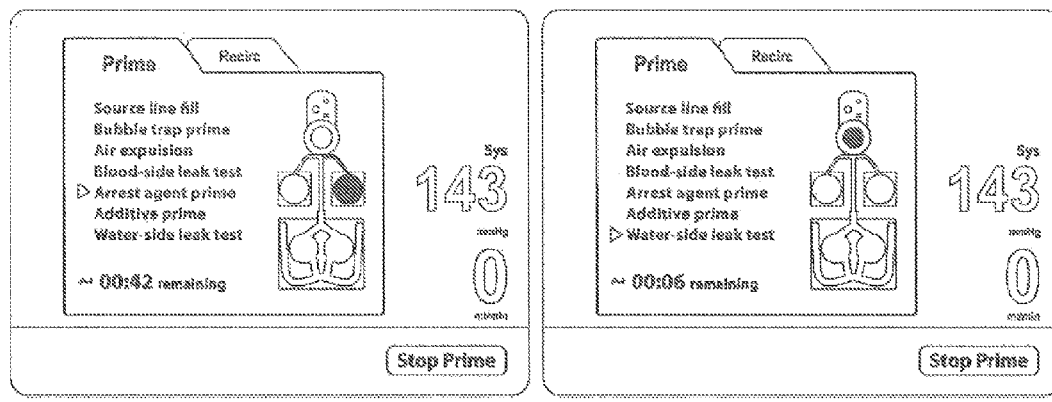
FIG. 8F   FIG. 8H
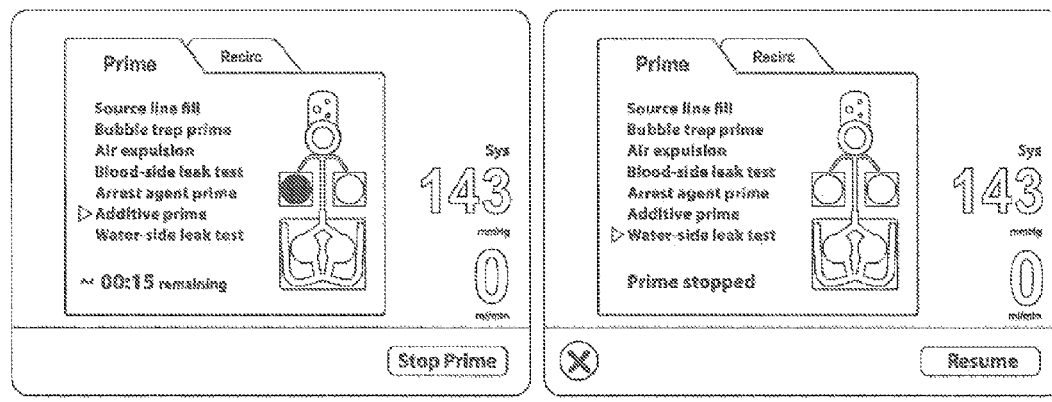
FIG. 8G   FIG. 8H-A

FIG. 11-5
FIG. 11-7
FIG. 11-6
FIG. 11-8

| Induction 71808 | |
|---|---|
| Arrest Conc - High (mEq/L) | 24 |
| Arrest Conc - Low (mEq/L) | 8 |
| Additive Conc (ml/L) | 8 |
| Blood : Cryst Ratio | blood |
| Cryst Bag Volume (ml) | 1000 |

| Induction 71808 | |
|---|---|
| Warm Temperature | 37°C |
| Start in | Cold |
| Circ System | Circ On |
| Heat Mode | 39°C Max |
| Cold Mode | Conserve Ice |

| Induction 71808 | |
|---|---|
| Arrest Conc - High (mEq/L) | 24 |
| Arrest Conc - Low (mEq/L) | 8 |
| Additive Conc (ml/L) | 8 |
| Blood : Cryst Ratio | blood |
| Cryst Bag Volume (ml) | 1000 |

| Induction 71808 | | |
|---|---|---|
| Warm Temperature | 37°C | |
| Start in | Warm | Cold |
| Circ System | Circ Off | Circ On |
| Heat Mode | 42°C Max | 39°C Max |
| Cold Mode | Continuous | Conserve Ice |

Induction 71808
Aorta Pressure (mmHg)

| Source | External | System |
|---|---|---|
| Upper Limit | 250 | 250 |
| Lower Limit | 10 | 10 |
| Auto Target | 80 | 350 |

Induction 71808
Retro Pressure (mmHg)

| Source | External | System |
|---|---|---|
| Upper Limit | 80 | 120 |
| Lower Limit | 10 | 10 |
| Auto Target | 35 | 50 |

Induction 71808
Vein Graft Pressure (mmHg)

| | |
|---|---|
| Upper Limit | 150 |
| Lower Limit | 10 |
| Auto Target | 120 |

Induction 71808

| | |
|---|---|
| VTBD Volume (ml) | 200 |
| VTBD Mode | Off |
| TTBD Time (min) | 1:30 |
| TTBD Mode | Off |
| Initial Ischemic Timer (min) | 15:00 |
| Repeat Ischemic Timer (min) | 2:30 |
| Ischemic Timer | Off |

6 of 8

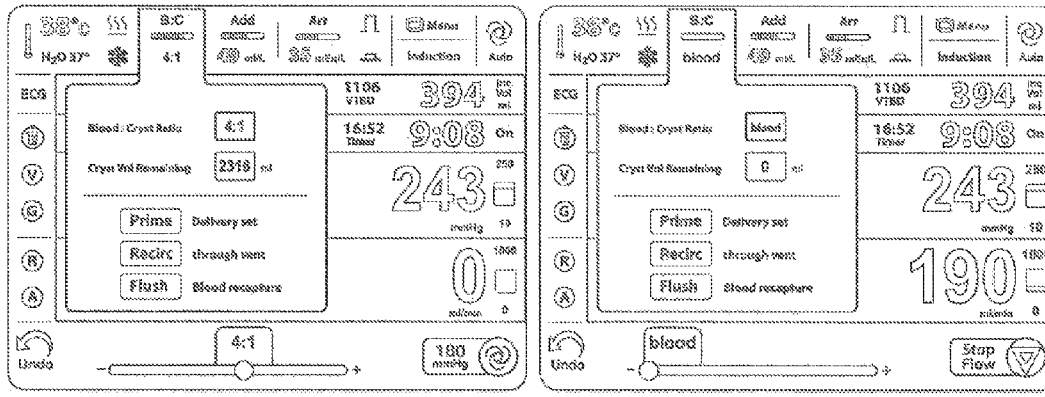
FIG. 15-26
FIG. 15-28
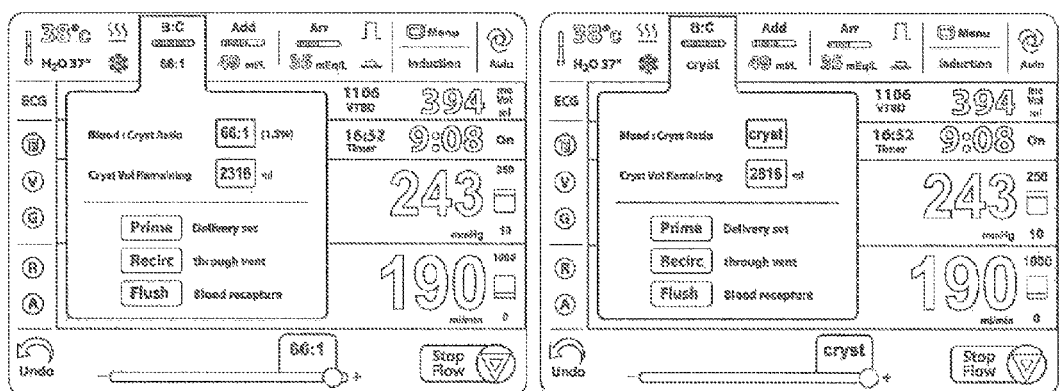
FIG. 15-27
FIG. 15-29

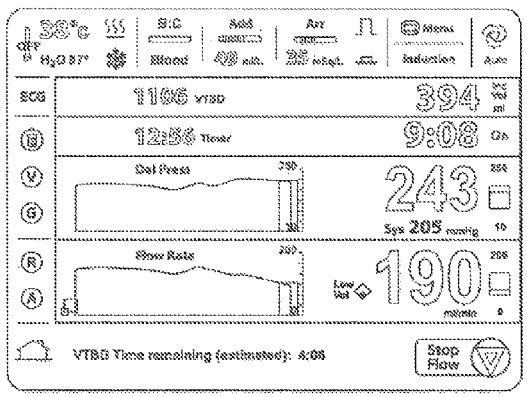
FIG. 15-3
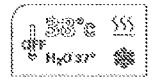
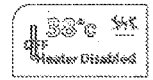
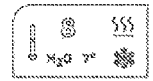
FIG. 15-31
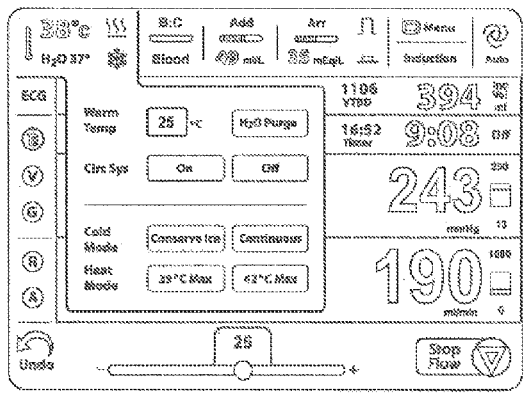
FIG. 15-30
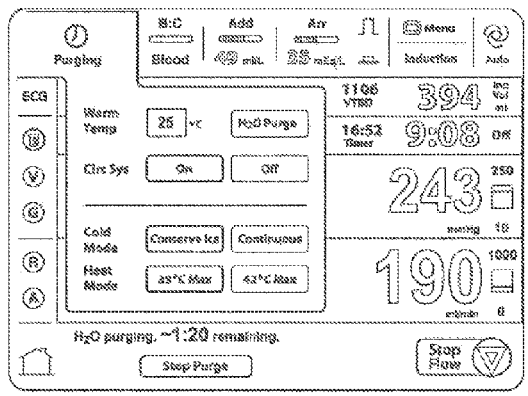
FIG. 15-32

CARDIOPLEGIA APPARATUS AND METHOD

CROSS-REFERENCE TO RELATED APPLICATIONS

This application claims the benefit of patent application, Ser. No. 61/534,110, filed Sep. 13, 2011, the disclosure of which is hereby incorporated by reference herein.

BACKGROUND OF THE INVENTION

Field of the Invention

This invention relates to a cardioplegia apparatus and method for automated arresting of a beating heart during cardiac surgery.

Description of the Related Art

In the performance of open heart surgery, the patient is supported by an extracorporeal blood circuit employing a heart/lung machine. The heart is isolated from the vascular system, and venous blood is diverted into the extracorporeal blood circuit where it is oxygenated, temperature-controlled and returned to the patient's arterial side. A separate circuit is established for supplying a cardioplegia solution to the heart as the surgery proceeds.

The cardioplegia circuit functions to still the heart, lower the metabolic requirements of the heart, protect the heart during periods of ischemia and, finally, prepare the heart for reperfusion at the end of the procedure. Operation of the extracorporeal blood circuit as well as the cardioplegia delivery is performed by a trained perfusionist under the direction of the surgeon. The principal elements of cardioplegia solution are blood, representing a small fraction diverted from the output of the heart/lung machine, combined with a crystalloid solution. In addition, an amount of potassium solution is added to the cardioplegia flow to still the heart.

Depending upon the requirements of the particular surgery, the cardioplegia solution may be cooled or warmed, and may be delivered in antegrade fashion to the aortic root or coronary ostia, or in a retrograde mode to the coronary sinus. The requirements placed upon the cardioplegia solution vary as the surgery proceeds, and are subject to the clinical judgment of individual surgeons.

By way of background, an early cardioplegia delivery system typically employed two tubes supplying the blood solution and the crystalloid solution respectively that were routed through a single rotary peristaltic pump whereupon the separate blood and crystalloid solutions in the respective tubes were combined into a single flow delivery line. The ratio between the blood solution and the crystalloid solution was determined by the relative diameters of the respective tubing carrying the two solutions, since each was mounted on the same rotary peristaltic mechanism and thus was forwarded by the same action. The tubing was usually provided in a 4:1 ratio of blood-to-crystalloid cross-sectional flow area, so that the rotary peristaltic pump would be delivering the blood solution and the crystalloid solution to the delivery line in a ratio of approximately 4:1. Potassium was typically provided to the delivery line upstream of the pump from two alternate crystalloid solutions containing potassium, one having a relatively low concentration of potassium, the other a higher concentration. The higher potassium concentration was utilized to arrest the heart, while the lower was used to maintain the stilled condition. While monitoring of the patient's condition during surgery, the perfusionist would select the higher concentration to provide sufficient potassium in the cardioplegia solution to establish the stilled condition of the heart and then select the lower concentration to maintain the heart in a stilled condition. The perfusionist would minimize the delivery of excessive potassium thereby minimizing the risks associated with hyperkalemia.

Early cardioplegia delivery systems were characterized by poor adaptability to varying requirements as may be required by the surgeon during surgery, such as the ratios of the solutions in the delivery flow and the control of the temperature of the delivery flow. The systems suffered from particularly poor control over the cardioplegia delivery flow at low flow rates. Moreover, the blood in the cardioplegia line was subjected to the peristaltic pumping action that produced shearing forces on the blood, thereby risking damage to the blood.

Representative early cardioplegia apparatuses and methods are disclosed in the following United States Patents (and Technical Disclosure), the disclosure of each of which is hereby incorporated by reference herein:

| Pat. No. | Title |
| --- | --- |
| T994001 | Hypothermic cardioplegia administration set |
| 4,416,280 | Cardioplegia delivery system |
| 4,568,330 | Cardioplegia delivery system with improved bubble trap |

One embodiment of an improved cardioplegia apparatus and method that has achieved substantial commercial success is known as the Myocardial Protection System sold under registered trademark "MPS" by Quest Medical, Inc., the assignee of the present invention. The functionality of Quest's MPS Myocardial Protection System is disclosed in U.S. Pat. No. 5,385,540, now Reissue U.S. Pat. No. 36,386, entitled Cardioplegia Delivery System, the disclosure of which is hereby incorporated by reference herein.

Quest's MPS Myocardial Protection System included an extracorporeal blood circuit having a first tube that was connected in fluid communication with a heart/lung machine to divert a portion of the blood flow from the heart/lung machine. A first pump combined blood from the first conduit with a crystalloid solution, and delivered the combined flow into a delivery line. The delivery line was connected in heat-exchanging communication with a heat exchanger to control the temperature of the cardioplegia in the delivery line. A second pump was provided for delivering a potassium solution into the delivery line downstream from the first pump at a flow rate less than 10% of the flow rate of the combined output of the first pump.

Quest's MPS Myocardial Protection System further included control means for adjusting the ratio of blood and crystalloid solution delivered by the first pump, for adjusting the total volumetric rate of flow from the first pump, and for controlling the operation of the second pump so that the volumetric rate of flow of the potassium solution was maintained at a selected percentage of the flow rate from the first pump.

In a preferred mode of operation of Quest's MPS Myocardial Protection System, the first pump employed two pumping chambers, so that one chamber could be refilled while the other was emptying, whereby substantially continuous flow from the first pump could be achieved. The second pump preferably comprised a positive displacement pump, either a syringe or a volumetric pouch configuration containing the potassium solution driven at a rate controlled by the control means. The output of the second pump joined the delivery line downstream from the first pump.

Quest's MPS Myocardial Protection System included a heat exchanger to both heat and cool the cardioplegia solution, and operated under the control of the control means. The first pump included at least one disposable in-line bladder and a separate drive means for changing the volume of the bladder. A fill cycle of the first pump comprised two separate time segments, including a first period for introduction of blood from the main extracorporeal blood circuit and a second period for the introduction of a second fluid, whereby the blood and the second fluid were combined in the bladder in a selected ratio before being forwarded from the first pump. The pressure of the cardioplegia solution was sensed, monitored, and controlled by the control means within safe operating limits.

Quest's MPS Myocardial Protection System further provided a disposable cassette including a delivery set for providing the medications to the patient. A representative cassette is more particularly described in U.S. Pat. No. 5,588,816, entitled Disposable Cassette for Cardioplegia Delivery System, the disclosure of which is hereby incorporated by reference herein.

As shown in FIG. 1A, a further improvement to Quest's MPS Myocardial Protection System involved a display control system (DCS), such as that disclosed in U.S. Pat. No. 5,573,502, entitled "Display Panel and Controls for Blood Mixture Delivery System", the disclosure of which is hereby incorporated by reference herein. All of the major operating conditions of Quest's MPS Myocardial Protection System including the desired volumetric rates, the desired ratios and percentages of blood, second fluid, third fluid, and any additional fluids, the output temperature and heating and cooling of the output fluid as well as the appropriate operating pressures and safety pressure conditions for either antegrade or retrograde cardioplegia, were conveniently controlled from the display panel connected to the cardioplegia system through a microprocessor control section. This advantageously freed perfusionists, surgeons and other healthcare professionals performing delicate medical procedures, from the complex, cumbersome and sometimes confusing manual rigging, connecting, heating, cooling, monitoring and adjusting of all the various aspects of the prior cardioplegia systems. The centralized control resulted in increased safety and quality of cardioplegia fluid delivery. The system was easily adaptable and adjustable to the particular requirements of a given patient.

While Quest's MPS Myocardial Protection System provided the surgeon with flexibility to continually change the mix, temperature, flow rate and precise quantities of medications delivered to the patient during open-heart surgery, the present invention provides substantial improvements to the functionality of Quest's MPS Myocardial Protection System. Further, as shown in FIG. 1B in comparison with FIG. 1A, the present invention provides a graphical user interface (GUI) to the Quest's MPS Myocardial Protection System.

Quest's MPS Myocardial Protection System comprised three sub-systems:
PMS—Pump Monitoring sub-system
PCS—Pump Control sub-system
DCS—Display Control sub-system The sub-systems PMS and PCS were dedicated to the pump operation whereas the DCS sub-system was dedicated to the User Interface consisting of LED's, switches, displays & knobs. As used herein, the MPS Console comprises a Pump Monitoring Subsystem (PMS) and a Pump Control Subsystem (PCS).

SUMMARY OF THE INVENTION

For the purpose of summarizing this invention, this invention comprises a software controlled device that incorporates a touch screen monitor that interfaces with a pump, temperature monitoring, pressure monitoring, a heat exchanger, an arrest agent pump, and an additive pump. Several notable features and programmable parameters are available, including:

On-demand variable ratio of blood:crystalloid
On-demand variable arrest agent concentration
On-demand variable additive concentration
On-demand warm/cold temperature control
Low Volume Mode (reduced priming volume)
Cyclic Delivery (variable amplitude, frequency and duty cycle)
Automatic priming and air detection/removal
Controlled pressure delivery
Pressure safety limits
Ischemic Timer
Protocol and Sequence options
Vein Graft labeling
View case history
Print case records
Display ECG
Electronic file transfer
Integrated safety mechanisms (visual and audible alarms)
PADCAB (beating heart surgery)

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENTS

Preferred Hardware Components of the Invention

Figures 1A, 1B:
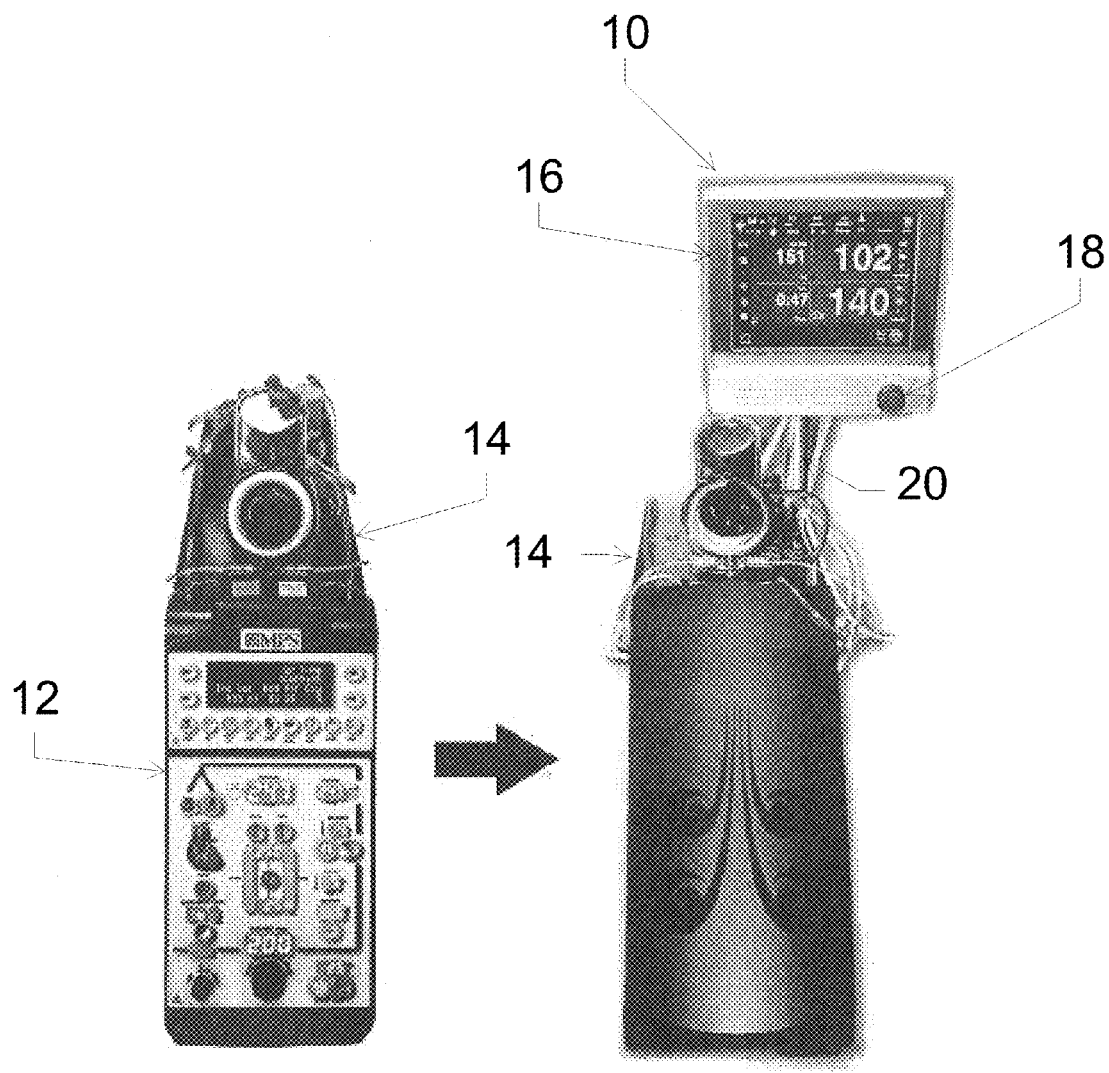
FIG. 1 is a visual comparison of the prior art to the present invention.

As best shown in FIG. 1B in comparison with FIG. 1A, a Microplegia Console Remote 10 (MCR Console) of the present invention replaces the Display Control System 12 (DCS) of Quest's existing Myocardial Protection System (MPS). The MCR Console 10 comprises an integrated LCD Display/Touch Screen 16 for displaying cardioplegia information and patient information to the perfusionist and allowing the perfusionist to input parameters via the LCD Display/Touch Screen 16 into the MCR Console 10 for computer-controlled perfusion of cardioplegia into the patient. The LCD Display/Touch Screen 16 includes a Flow Knob 18 that allows the perfusionist to manually control the cardioplegia flow rate. Preferably, manual control of the cardioplegia flow rate via the Flow Knob 18 takes precedence over any in-process computer-controlled cardioplegia perfusion into the patient. More preferably, manual control of the cardioplegia flow rate via the Flow Knob 18 suspends or cancels any in-process computer-controlled cardioplegia perfusion such that the perfusionist may immediately resume manual control of the cardioplegia perfusion into the patient.

As shown in FIG. 1B, the MCR Console 10 is preferably a physically separate console that is operatively interfaced (e.g., through RS485 interface) to the MPS Console 14 by an interface cable 20, thereby allowing, during a surgical operation, for the MCR Console 10 to be conveniently located in front of the perfusionist and for the MPS Console 14 to be located elsewhere in the operating room out of the way of the surgical team.

The interface cable 20 enables intercommunication of diagnostics status, messages and periodic data updates between the MCR Console 10 and the MPS Console 14. Also preferably, the MPS Console 14 provides electrical power to the MCR Console 10 via the interface cable 20 such that the MCR Console 10 may be "turned on" with the MPS power switch, thereby minimizing synchronization issues that might otherwise arise if the MCR Console 10 and the MPS Console 14 were not powered on simultaneously.

Figure 2:
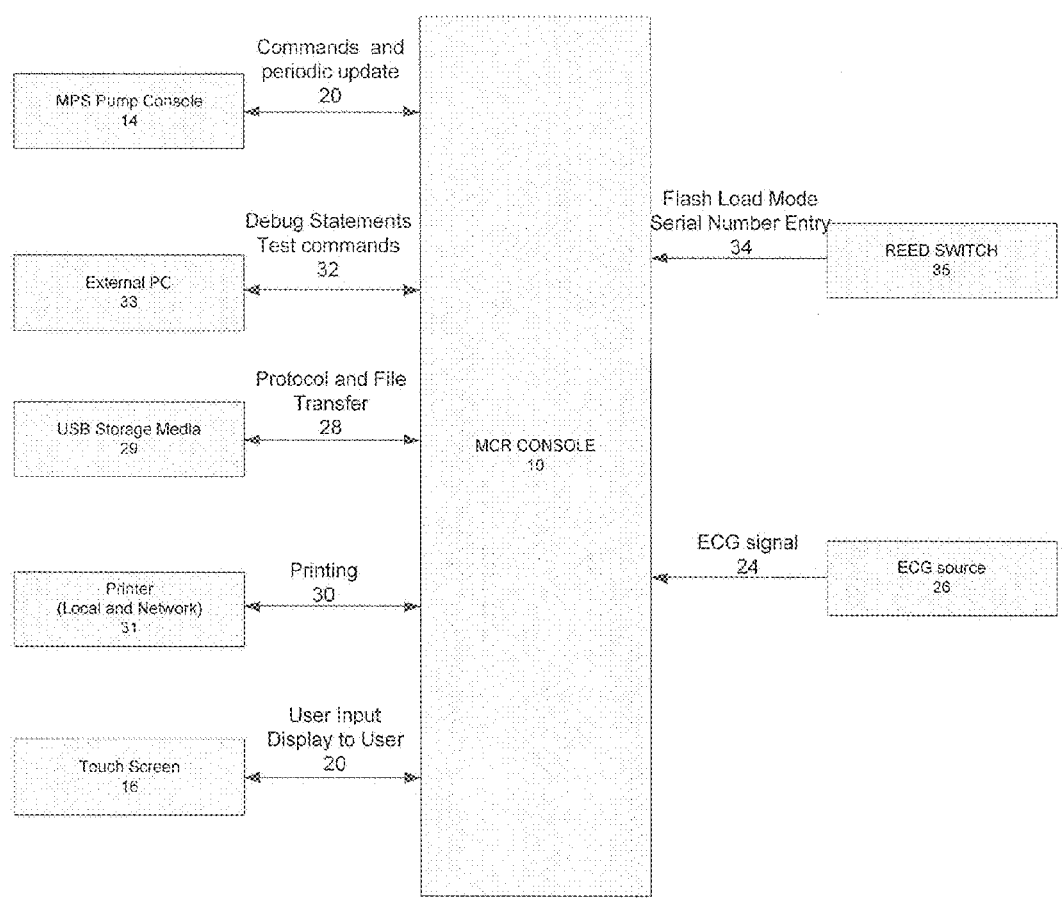
FIG. 2 is a block diagram of the MCR Console.

More particularly, referring to FIG. 2, the MCR Console 10 includes an ECG input 24 allowing a conventional ECG waveform from an electrocardiogram (ECG) source 26 to be displayed on its LCD Display/Touch Screen 16. Further, the MCR Console 10 may additionally include a conventional USB interface port 28 to export or import Protocols, Sequences, Dose Histories, Logs and other files (described hereinafter) to or from external storage media 29 (e.g., SD memory card), a conventional printer port 30 for network and local printing 31, a communication port 32 for connectivity communications (e.g., Bluetooth, WiFi, Ethernet) such as for interfacing with an External Personal Computer 33 for receiving test commands during system debugging. Finally, the MCR Console 10 includes a Reed Switch input 34 that detects when the contacts of a reed switch 35 are closed. The reed switch 35 is preferably concealed within the housing of the MCR Console 10 allowing a magnet to be placed on the outside of its housing proximate the reed switch 35. Using a magnet to close the contacts of the reed switch 35 provides, as described hereinafter, a way to boot the MCR Console 10 into a flash loader mode.

The present invention is preferably implemented on a computer hardware platform that executes software (described below). While many hardware platforms may suffice, a preferred architecture of the hardware platform is described in the block diagram of FIG. 3.

Preferred Software Implementation of the Invention

The method of the present invention is preferably software implemented. While many software platforms may suffice, a preferred software platform employs the operating system known as the QNX Neutrino RTOS. As illustrated in the functional decomposition diagram of FIG. 4, the software preferably comprises the various software modules that perform their respective functions described as follows:

| Module Name | Description |
|---|---|
| GUI | The GUI is responsible for, |
| | Facilitating the user to control and navigate to different functionality of the system through GUI screens |
| | Navigating to different internal states on either by system event or by user input |
| | Facilitating the user to edit and review the Case Manager including the Protocol Manager and Sequencer |
| | Facilitating the user to edit and review the system settings |
| | Facilitating the user to start new case or resume case and run |
| | Maintaining and managing internal states of the MCR Console depending on user navigation |
| | Facilitating to provide visual feedback for any notification with different options to respond |
| | Facilitating the user to intimate the errors created in the system, severity of the error. |
| | Facilitating the user to intimate the action to be taken incase of errors occurred |
| | Facilitating user to view the dose records and case history |
| | Facilitating the user to allow storing of the Log files, Case history, Dose records, Protocols and Sequences into the external storage media and vice versa |
| | Facilitating user to make print outs of the dose records into network or local printers. |
| | Supporting multiple language |
| | Entry and exit into screen saver mode |
| | Facilitating user to view the pressure and flow graphs and ECG strip chart while running the case |
| | Facilitating user to view calibration constants, device serial number and software versions of the different processors |
| Process Manager | The Process Manager is the first user module to be started on the MCR Console. The Process Manager is responsible for |

| Module Name | Description |
|---|---|
| | Spawning either Comm. Manager or Simulator process depending on cable connected<br>Spawning all other processes in MCR Console<br>Monitor all other user processes through a "Health check" message, every 5 second. If any processes fail to send a response to this message, it is inferred that software is malfunctioning.<br>Maintaining the overall state of the MCR Console.<br>Power On Self Test (CPU instruction and RAM Read/Write Test) in the MCR Console<br>Coordinating diagnostics activities with MPS Console 14 and updating status to the user<br>Calculating and verifying checksum over entire flash memory |
| Communication Manager | The Communication Manager is responsible for,<br>Interacting with MPS Console 14 sub system through RS485 protocol<br>Validates the data received from the MPS Console 14 and sends response to the MPS Console 14<br>Handling Ring concept to communicate with PCS and PMS subsystem on the RS485 node<br>Handling Error detection mechanism to identify the errors during communication with MPS Console 14<br>Handling error recovery mechanism to recover-from the communication errors with MPS Console 14<br>Queuing the communication messages into transmit or receive queue<br>Sending or receiving messages between MPS Console 14 and all other processes in MCR Console |
| Data Manager | The Data Manager is responsible for,<br>Maintaining Case History and Dose Records<br>Maintaining Error logs<br>Storing and retrieving system settings and case parameters in the EEPROM<br>Maintaining protected mirror data of critical parameters |
| Device Manager | The Device Manager is responsible for,<br>Facilitating user to use local or network printer<br>Facilitating to print the dose history and dose records<br>Facilitating to store the Log files to the external storage media<br>Facilitating to store the Case History files to the external storage media<br>Facilitating to store and get the protocols to/from external storage media<br>Facilitating to Delete the Protocol and Case History files from the external storage media<br>Facilitating to print Debug information and receive Test commands from external PC<br>Managing the File Transfer of protocols and Case history between Storage Media and Quest system and vice versa<br>Detecting the storage media and check compatibility |
| Alarm | The Alarms is responsible for,<br>Maintaining and managing alarms for the errors sent by MPS Console 14 and internal errors in the MCR Console<br>Facilitates to play different audio depends on alarm type and severity.<br>Playing wave files depending upon the severity of the Alarms created<br>Providing audible feedback when the user presses valid and invalid key press<br>Providing audible feedback when user ack. for the notification messages<br>Facilitating user to adjust the Audio volume level of the speaker |
| ADIO | The ADIO runs in user space as process and it is responsible for,<br>Read the Flow Knob 18 rotation<br>Process ECG ADC input<br>Read/control GPIO input/output |
| SIMULATOR | The Simulator process is spawned only when MCR Console finds hardware dongle attached to communication port between MCR Console and MPS Console 14. In this case Communication Manager process is not spawned. The Simulator process responsible for simulating the MPS Console 14 data and message flow to the MCR Console. |

Preferred Graphical User Interface (GUI) of the Invention

While many software graphical user interfaces (GUI) may suffice, the preferred GUI of the LCD Display/Touch Screen 16 of the invention comprises Photon microGUI which is integrated with the QNX Neutrino RTOS operating system.

Figure 5:
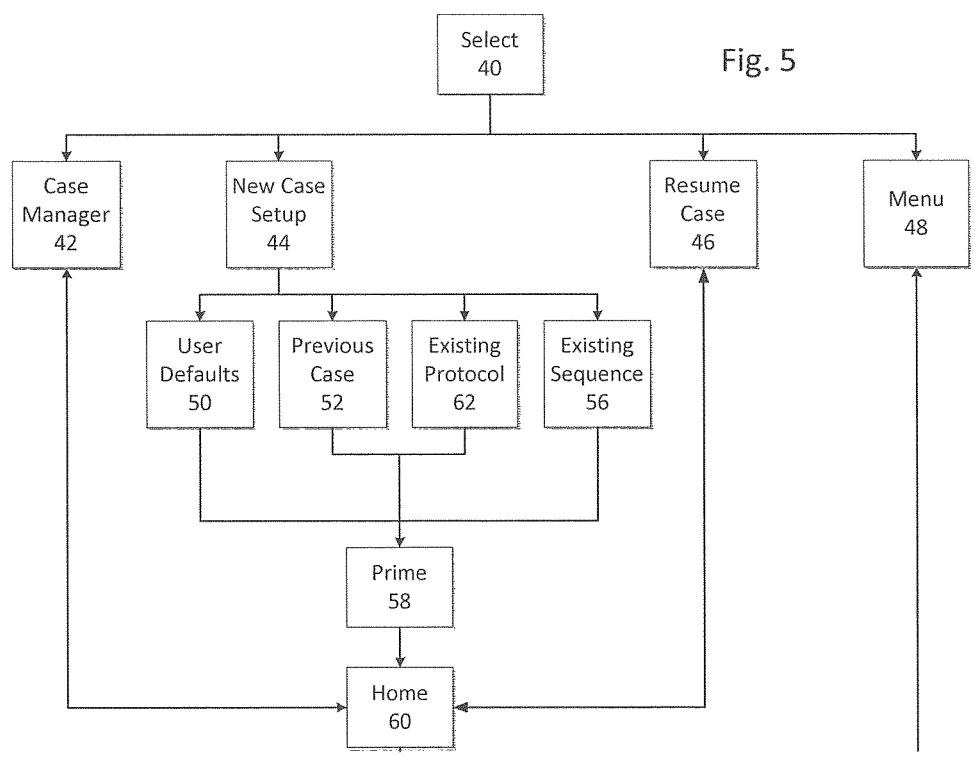
FIG. 5 is a block diagram of the GUI interface of the MCR Console.

A functional overview of the various steps of the GUI of the present invention is illustrated in the block diagram of FIG. 5.

More particularly, unless the MCR Console 10 has booted into the flash loader mode or in the simulator mode upon power-up (described below), the perfusionist is first presented with a Select Step 40 allowing selection of a Case Manager Step 42, a New Case Setup Step 44, a Resume Case Step 46 or a Menu Step 48. As described in detail below in connection with their respective GUI Screens, the Case Manager Step 42 allows the perfusionist to setup "protocols" and then "sequence" them in a specific order for a particular patient. New Case Setup Step 44 allows the perfusionist to setup for a new patient based upon User Defaults 50, the Previous Case 52, an Existing Protocol 54 or Existing Sequence 56. After setting up for a new patient, a Prime Step 58 primes the MPS Console 14 to begin perfusion. After priming, a Home Screen Step 60 allows the perfusionist to monitor the computer-controlled delivery of cardioplegia to the patient throughout the surgical procedure.

While in the Home Screen Step, 60 the perfusionist may manually pause or stop the delivery of cardioplegia to the patient in which case the Resume Case Step 46 allows the perfusionist to easily resume the case. Also, while in the Home Screen Step 60, the perfusionist may return to the Case Manager Step 42 to temporarily change (i.e. "tweak") the previously-setup protocol or sequencing parameters. Finally, while either in the Select Screen Step 40 or while in the Home Screen Step 60, the perfusionist may select the Menu Screen Step 48 to perform various administrative functions (e.g., Case History, File Transfer, etc. as described below)

Each of the Steps 40-60 are displayed on the LCD Display/Touch Screen 16 to the perfusionist via various GUI "screens." The screens display, via active or passive icons, the appropriate controls and parameters relevant to the step being performed. Being a touch screen, the active icons representing such controls and parameters may be selected by the perfusionist as desired for manipulation of the parameters or navigation to previous or succeeding screens. It is noted that as used herein, the term "active icon" means that the icon may be "selected" by the user touching it on the screen, allowing selection of the parameter or allowing navigation, depending on the context in which the active icon is employed. While many variations in the screens may suffice, the screens of the preferred embodiment of the present invention are illustrated in FIG. 6 through FIG. 17. They are described in detail as follows.

Select Step 40

Figure 6:
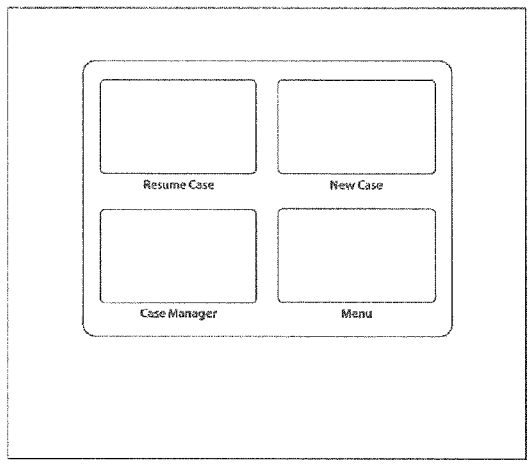
FIGS. 6-17 are the various screens of the preferred embodiment of the GUI interface of the MCR Console.

During the Select Step 40, the Select Step Screen shown in FIG. 6 is displayed on the LCD Display/Touch Screen 16. The Select Step Screen includes Resume Case, New Case, Case Manager and Menu active icons that may be selected by the perfusionist as desired and activated to transition to the step thus selected.

New Case Setup Step 44

Figures 1A, 7:
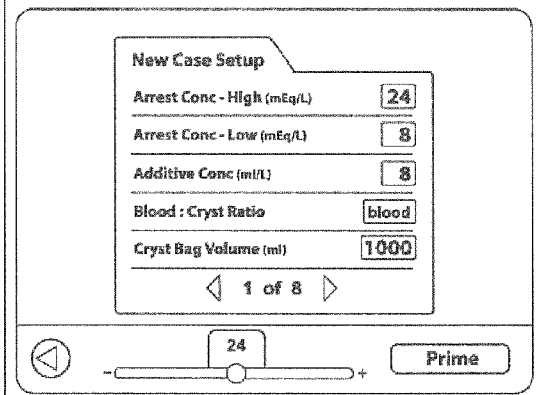
Figures 1, 7:
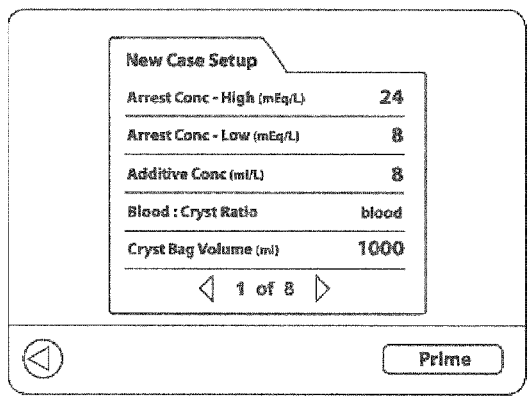
Figures 2, 7:
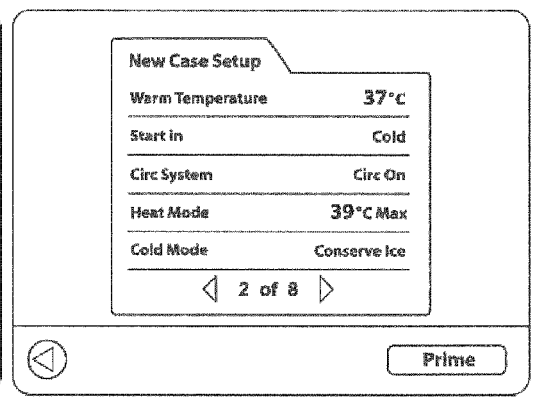
Figures 7A, 7C:
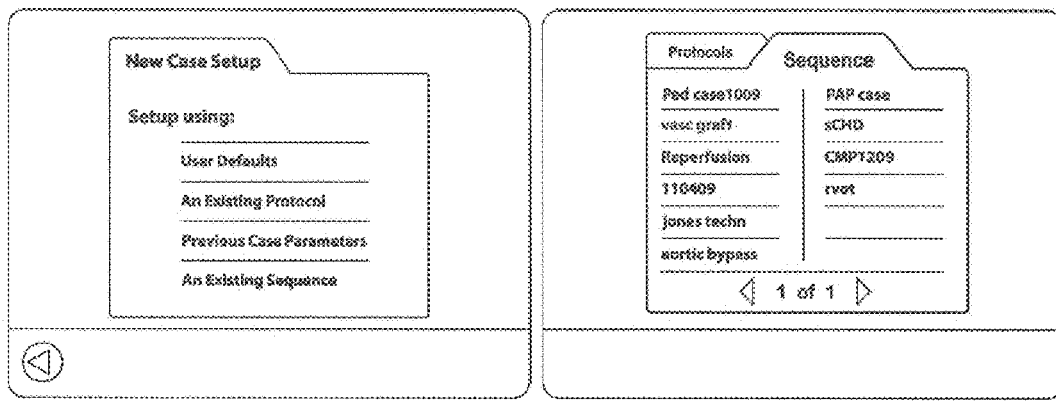

Upon activating the New Case icon, the New Case Setup Screen shown in FIG. 7A is displayed on the LCD Display/Touch Screen 16. The New Case Setup Screen 16 includes User Defaults, An Existing Protocol, Previous Case Parameters and An Existing Sequence active icons (corresponding to the User Defaults, Previous Case, Existing Protocol and Existing Sequence Steps 50, 52, 54 and 56 respectively) that may be selected by the perfusionist as desired and activated to transition to the step thus selected.

The perfusionist's selection of the User Default active icon, displays the Review/Modify Parameter screens of FIGS. 7-1—7-8A, which may be scrolled through to display the factory-predefined user default parameters such as those reflected in the following table:

| Name | Range | Factory Default |
|---|---|---|
| Arrest Conc - high | 0-40 | 24 |
| Arrest Conc - low | 0-40 | 8 |
| Additive Conc | 0-50 | 8 |
| Blood:Cryst Ratio | blood, 66:1, 49:1, 39:1, 32:1, 27:1, 24:1, 21-2:1, 1:1, 1:2-9, cryst | blood |
| Cryst bag volume | 0-3000 | 1000 |
| Warm Temperature | Off, 4-39(41) | 37 |
| Start in | Warm, Cold | Cold |
| Circ System | ON, OFF | ON |
| Heat Mode | Normal, Extended | Normal |
| Cold Mode | Conserve Ice, Continuous | Conserve Ice |
| Ante Pressure Source | External, System | System |
| Upper Ante Ext Press Limit | 1-250 | 250 |
| Lower Ante Ext Press Limit | 0-200 | 10 |
| Ante Ext Target Pressure | 1-250 | 80 |
| Upper Ante Sys Press Limit | 1-500 | 400 |
| Lower Ante Sys Press Limit | 0-350 | 10 |
| Ante Sys Target Pressure | 1-500 | 350 |
| Retro Pressure Source | External, System | System |
| Upper Retro Ext Press Limit | 1-125 | 80 |
| Lower Retro Ext Press Limit | 0-80 | 10 |
| Retro Ext Target Pressure | 1-125 | 35 |
| Upper Retro Sys Press Limit | 1-500 | 80 |
| Lower Retro Sys Press Limit | 0-350 | 10 |
| Retro Sys Target Pressure | 1-500 | 35 |
| Upper Vein Graft Press Limit | 1-200 | 150 |
| Lower Vein Graft Press Limit | 0-120 | 10 |
| Vein Graft Target Pressure | 1-200 | 120 |
| VTBD Volume | 10-4000 | 200 |
| VTBD Mode | Once, Always, Off | Off |
| TTBD Time | 1:00-15:00 | 1:30 |
| TTBD Mode | Once, Always, Off | Off |
| Initial Ischemic Time | 1-20 | 15 |
| Repeat Ischemic Time | 1-20 | 2 |
| Ischemic Timer | On, Off | Off |
| Initial Del Route | AORTIC DEL, RETRO DEL, ANTE RETRO DEL | AORTIC DEL |
| Del Line Type | SINGLE, DOUBLE | SINGLE |
| Initial Arrest Mode | High, Low | High |
| Flow Mode | Normal, Low Vol, Always Cyclic | Normal |
| Flow Knob Sensitivity | 10, 25, 50, 75, 100, 125, 150, 175, 200 | 100 |
| Audible Tones | OFF, LOW FREQ, NORMAL | NORMAL |
| Language | ENGLISH, JAPANESE | ENGLISH |
| Off Time Delay | 1-60 | 20 |
| Home View | Charts, Zoom | Charts |
| Arrest Source Unit | mEq, mMol | mEq |

The default parameters are presented to the perfusionist for review and if desired, modification (i.e., tweaking) of the default parameters within the factory-preset ranges or options set forth in the above table. For modification of numerical parameters, the parameter is selected whereupon a slider bar is presented in the lower portion of the screen showing the current numerical value of the parameter. As the perfusionist slides the slider left to decrease or right to increase the numerical value as desired, the value displayed changes accordingly. The length of travel of the slider is limited to the factory default ranges set forth in the above table. For example, FIG. 7.1A shows the Arrest Concentration parameter highlighted allowing it to be modified from its factory default of 24 to a value within the range of 0-40. For modification of parameters having two or more modes, selection of the parameter produces a "fly-out" list of options to be displayed, allowing the perfusionist to select one. For example, FIG. 7-2A shows the Start In parameter's two modes "Warm" and "Cold" being presented for selection by the perfusionist.

Each of the Review/Modify Parameter screens of FIG. 7 includes a Prime active icon (corresponding to the Prime Step 58). After the perfusionist has reviewed or modified the parameters via the Review/Modify Parameter (FIG. 7) as desired, the perfusionist may select the Prime icon to transfer to the Prime Step 58 (described below) in preparation for delivering cardioplegia to the patient under the constant monitoring of the perfusionist during the Home Step 60 (described below).

At the conclusion of each case, the parameters used during that case are stored in memory as the Previous Case Parameters. As an alternative to displaying the User Default parameters described above in the Review/Modify Parameter screens of FIG. 7, the perfusionist may select Previous Case Parameters whereupon the previous-case parameters are displayed in the Review/Modify Parameter screens of FIG. 7 allowing the perfusionist to review or modify them as desired, and when completed, transfer to the Prime Step 58 in preparation for delivering cardioplegia to the patient under the constant monitoring of the perfusionist during the Home Step 60 (described below).

The apparatus and method of the invention allows the perfusionist to predefine a collection of case parameters, label them and store them in memory for later use (via Case Manager 18 described below). These pre-defined collections of case parameters are referred to herein as "Protocols". In lieu of using User Default or Previous Case parameters (corresponding to the User Default Step 50 or Previous Case Step 52), the perfusionist may select An Existing Protocol in the New Case Setup screen 16 (corresponding to the Existing Protocol Step), whereupon a listing of the predefined Existing Protocols is presented (see FIG. 7B). Upon selection of the desired Existing Protocol active icon, its pre-defined parameters may be presented in the Review/Modify Parameter screens of FIG. 7 allowing the perfusionist to review or modify them as desired, and when completed, transfer to the Prime Step 58 in preparation for delivering cardioplegia to the patient under the constant monitoring of the perfusionist during the Home Step 60 (described below).

The apparatus and method of the invention 10 allows the perfusionist to sequence a series of Protocols to be used in sequence, label them and store them in memory for later use (via Case Manager 18 described below). These pre-defined collections of Protocols are referred to herein as "Sequences". The perfusionist may select An Existing Sequence in the New Case Setup screen (FIG. 7A), whereupon a listing of the pre-defined Existing Sequences are displayed (see FIG. 7C). Upon selection of the desired Existing Sequence, its sequence of Protocols may be presented in (see Case Manager screens) allowing the perfusionist to review or modify them as desired (and to review or modify the Protocols thereof through the Review/Modify Parameter screens of FIG. 7), and when completed, transfer to the Prime Step 58 in preparation for delivering cardioplegia to the patient under the constant monitoring of the perfusionist during the Home Step 60 (described below).

Prime Step 58

Figure 9:
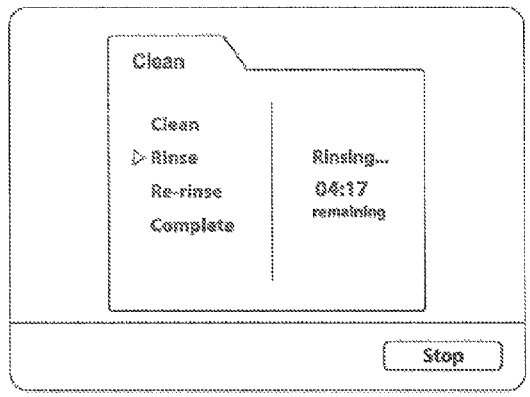
Figures 1, 9:
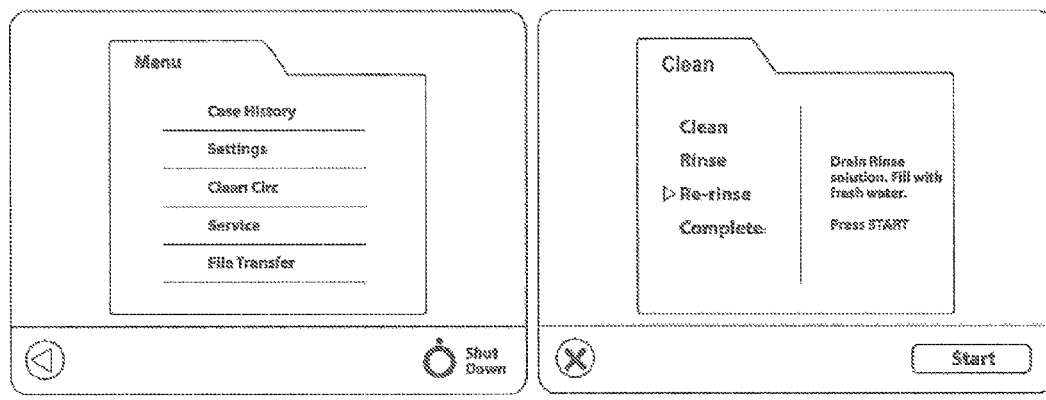
Figures 9, 10:
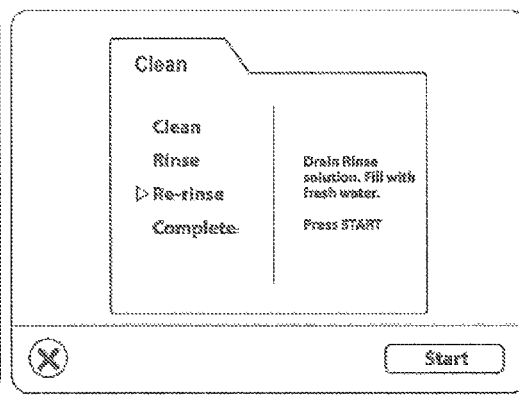
Figures 9, 10, 11, 12, 13, 14, 15, 16, 17, 18, 19:
Figures 6, 8, 9:
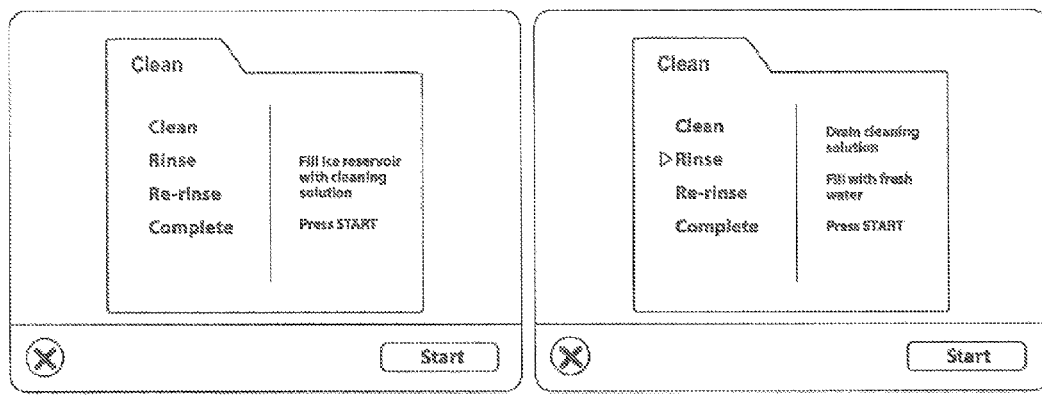

Upon selection of the Prime icon to transfer to the Prime Step 58, priming of the disposable cassette begins and is presented graphically to the perfusionist via the Prime screens of FIG. 8. Starting the prime process sends an auto enable message to the MPS Console 14 to initiate the auto prime process. The auto prime process takes approximately 2 minutes and comprises 10 sub-steps, each received from the MPS Console 14 and used to update the Prime screen. The expected duration of each step is also received from the MPS Console 14 and is used to update the remaining time at the start of each step. The following table sets forth each of the preferred sub-steps of the Prime Step and the Cumulative Re-sync Time

|   | Sub-Steps | Cumulative Re-sync Time (seconds) |
|---|---|---|
| 0 | NA (ignore) | NA |
| 1 | NA (ignore) | NA |
| 2 | Source Line Fill | 130 |
| 3 | Fluid Level Check | 100 |
| 4 | Air Expulsion | 95 |
| 5 | NA (ignore) | NA |
| 6 | Blood Leak Test | 70 |
| 7 | Arrest Agent Prime | 50 |
| 8 | Additive Prime | 30 |
| 9 | Water Leak Test | 10 |

Referring to the sequential iterations of the Prime screen of FIG. 8, the auto prime progress is displayed under a Prime Tab listing the sub-steps from the above table (along with the System Pressure and Flow Rate). The sub-steps are sequentially highlighted to show the sub-step in progress and to display a corresponding graphic for that step, while updating the countdown time shown in the message window. The perfusionist may select a Stop Prime active icon to stop automatic priming, whereupon a Resume Prime active icon and a Cancel active icon (shown as an X) are displayed (see for example FIG. 8H compared with 8H-A). Selection of the Resume Prime active icon resumes automatic priming whereas selection of the Cancel icon sends a manual enable message to the MPS Console 14 and transfers the process to the Recirc Tab of the Prime Screen (see FIG. 8I) allowing the perfusionist to manually control the priming via the Flow Knob 18. The perfusionist may select a Done active icon when manual control is completed, whereupon the process transfers to the Home Step 60 starting the delivery of cardioplegia to the patient.

Menu Step 48

During the Menu Step 48, a Menu Screen is displayed allow the administrative functions of Case History, Settings, Clean Cir, Service and File Transfer that the perfusionist may perform (See FIG. 9-1).

Figure 3:
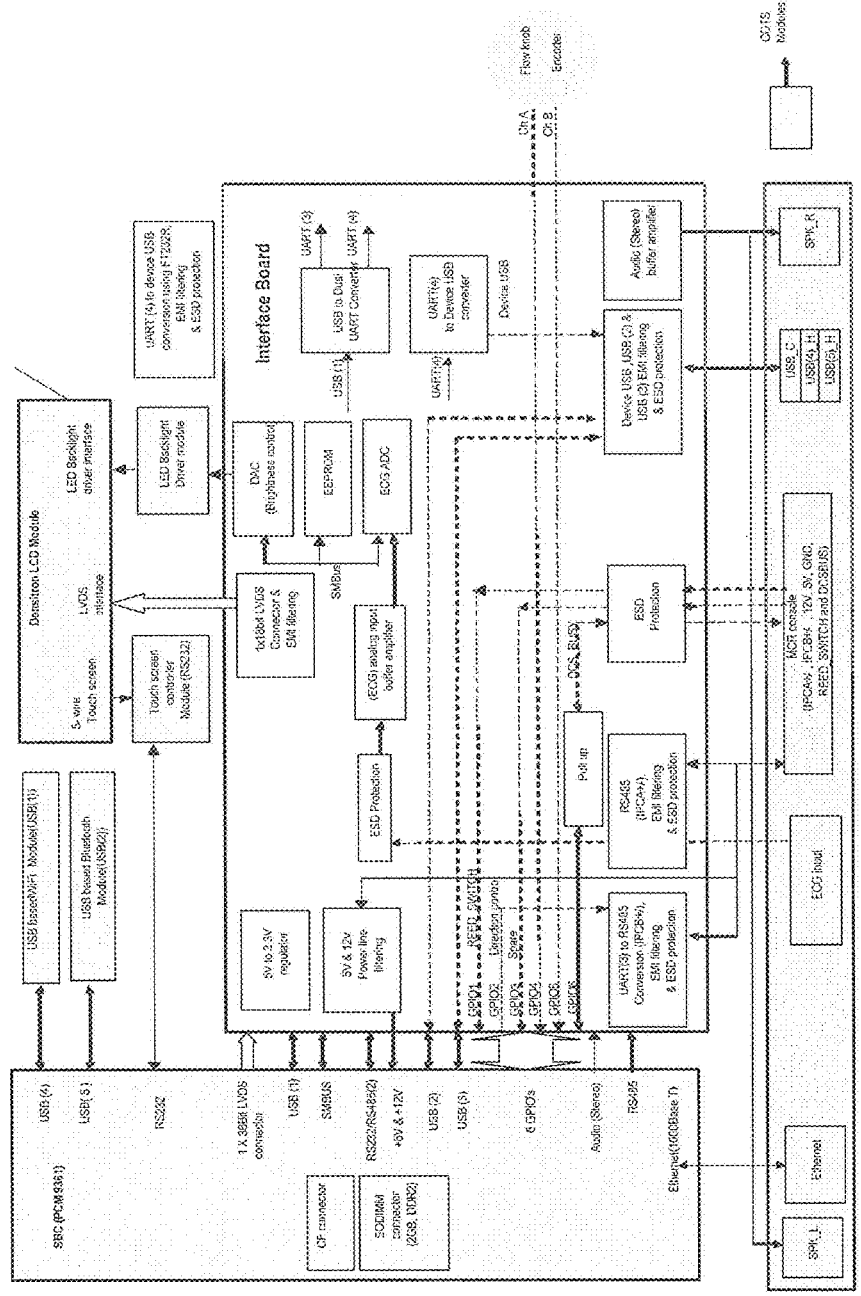
FIG. 3 is a block diagram of the hardware components of the MCR Console.
Figure 4:
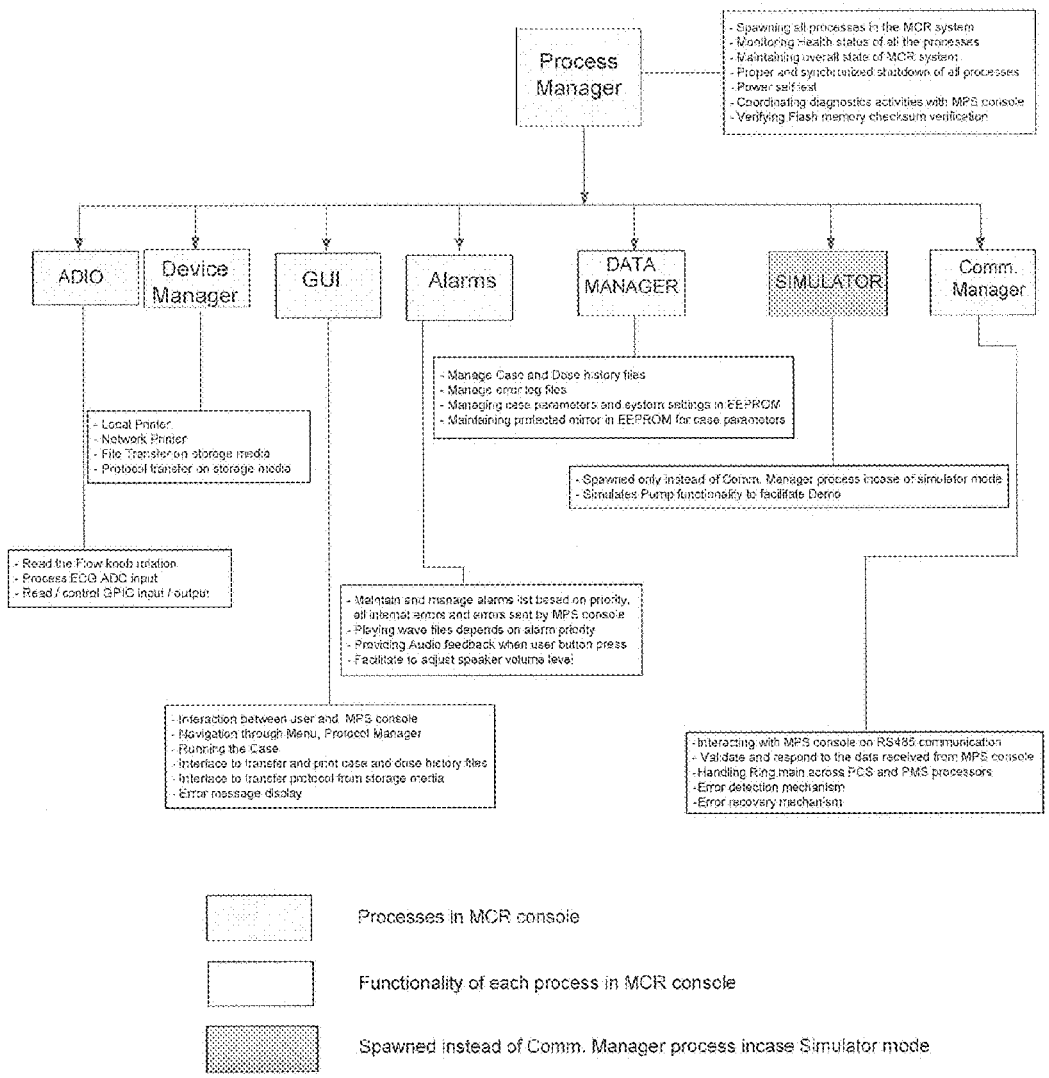
FIG. 4 is a functional decomposition diagram of the MCR Console.

More specifically, selecting the Settings active icon in FIG. 9-1 presents the Settings screens of FIGS. 9-2 & 3 allowing setting of the LCD Brightness, Speaker Volume, Flow Knob sensitivity, Printer, Date, Time and Language. As shown in FIGS. 9-4 & 5, the Printer may comprise a local printer or a network printer.

Selecting the Clean Circ active icon in FIG. 9-1 displays the Clean screen of FIG. 9-6 which, upon pressing a Start active icon, sends a circ clean message to the MPS Console 14 to begin the cleaning step. The process then proceeds to a rising step which, upon pressing of the Start active icon, sends a rinse message to the MPS Console 14 to being rising. Finally, the process continues to a re-rinse step which, upon pressing of the Start active icon, sends a rinse message to the MPS Console 14 to being re-rinsing. Each step in progress is received from the MPS Console 14 and is used to update the sequential highlighting of the corresponding active icon and to display a corresponding instructional message for each such step (see FIGS. 9-7 through 9-13). The time remaining is preferably shown.

Selecting the Service active icon in FIG. 9-1 displays the Service screens of FIGS. 9-14 & 9-15 allowing setting of the serial number (preferably by holding a hidden active icon for a period of time (e.g., three seconds) while the REED_SWITCH signal is active. Service Codes are displayed including the 30 most recent error codes as a scrollable list with the Error Code in the first column and the Reason Code (if applicable) in the second column. The "Arr piston" and "Add piston" info displays the Arrest and Additive maximum piston travel steps. The Software Version Info displays the Software build date and time for all 3 processors. The Calibration Data (Gain, Offset, Res1, Res2, Circ, Deliv) shows the calibration constants for all pressure and temperature sensors in the MPS Console 14. Selecting the Print active icon prints the entire screen. Selecting the Get Logs active icon results in the transmission of all log data through the console's serial RS232 communication port (see FIG. 9-15), whereupon the USB port is monitored and a message is displayed notifying the user that the log data is being received. Upon storage of the data, a message notifies the user to insert Storage Media and press copy, whereupon the data is copied to removable media.

Selecting the Case History active icon in FIG. 9-1 presents the Case History screens of FIGS. 9-16 through 9-21. As shown in FIG. 9-16, a list of the most recent Case records are identified by their start date and time. If an external storage device is plugged in, the storage icon is shown. An individual case may be dragged and dropped into the storage icon which will result in copying all the Dose Records and Pressure-Flow Data associated with that Case into the external storage device.

The Dose History screen of FIG. 9-17 shows a table where each row or record corresponds to a dose. Every dose record for the case is shown in the table (the table may be scrollable). The patient ID is displayed if available. The Dose History table preferably has the following fields:

Date/Time—This field shows the date and time corresponding to the start of the record. If a Note had been previously entered for this record, the Note icon is shown.

On Time—This field shows the On Time for the dose in MM:SS format.

Arrest—This field shows the Arrest Volume delivered of Potassium Chloride delivered.

Additive—This field shows the Additive Volume delivered.

Temperature—This field shows the last sampled delivery temperature for the dose in ° C.

Volume—This field shows the total delivered volume for the dose in ml.

Route—This field shows the last route selected in the dose. The possible values for this column are A (Antegrade), R (Retrograde) or S (Simulgrade).

VG/Conduit—This field shows the Vein Graft and the Conduit label if it had been named previously. If Vein Graft mode was activated but never labeled, "VG" may be used as the default label. This field may be blank when Vein Graft mode is not activated. Selecting this field allows the user to name or rename the Vein Graft. Selecting the VG/Cond field transitions to the screen of FIG. 9-18 whereas selecting any other field of the dose record transitions to the screen of FIG. 9-19.

Selecting the Print active icon prints the entire table along with all added notes preceded by its corresponding date/time entry.

As shown in the screen of FIG. 9-18, the VG Label options are presented allowing the perfusionist to select from two different lists to label the Vein Graft—one selection from the Conduit list and one from either the Left or Right Graft list. If the Vein Graft had already been labeled these labels may be shown selected upon entering this state. If not previously labeled (blank field), the labels are not shown as being selected. Only one selection (or no selection) is allowed in each list. Selecting a selected label deselects it. When Confirm is selected, the label is added to the Dose Record and displayed in the Dose History Table.

In the Dose Record screen of FIG. 9-19, the selected Dose Record from the table in the Dose History View is displayed below the column headings. Any previously added note may also be displayed. The Pressure and Flow Data corresponding to the selected dose is displayed as two separate graphs—preferably the X axis being the On time and the Upper Limit on the Y axis auto scaling according to the corresponding max Y value (e.g., every data point (sampled every 4/8 second for flow, and every 1/8 second for pressure) of the pressure (delivery pressure) and flow (calc Flow) data received from the MPS Console 14 during the dose being stored in non-volatile RAM). A single dose is preferably limited to a maximum of 4 hours (looped data). The data corresponding to the 'off time delay' that follows the end of every dose need not be displayed. The dose and case separators may also be stored in memory. Preferably, data from the most recent cases is saved. A ruler slider may be shown at the bottom of the page to zoom in or zoom out the X axis. Two arrows are initially shown at either end of the scale with the scale starting at 0 seconds and ending at the dose duration. As an example, a dose that started at 6:30:20 and ended at 6:33:25 has a start value of 0 and an end value of 3:05. Sliding the left arrow has the effect of manipulating the starting X value. Sliding the right arrow has the effect of manipulating the ending X value. Inasmuch as both graphs share the same X axis, the same effect shall be seen on both graphs simultaneously. The x-axis re-scaling occurs dynamically as the arrows are being adjusted. Finally, selecting a Print active icon prints the displayed page.

As shown in the Dose Record Note screen of FIG. 9-20, an on-screen keyboard is displayed allowing the perfusionist to enter case notes. Similarly, the Edit Patient ID screen of FIG. 9-21 allows editing of the patient identification (e.g., name).

Upon selection of the File Transfer active icon in FIG. 9-1, listings of Case Histories and Protocols [and Sequences] are displayed in respective tabbed windows (see FIGS. 9-22 & 23). Selection of one of the tabbed windows (e.g., Case History in FIG. 9-22 or Protocols in FIG. 9-23), displays the Cases or Protocols in one or more screens. One or more of the Protocols but preferably only one of the Cases may be selected (i.e., highlighted) and then copied to removable media (if installed) or transferred to an entity (e.g., Quest Medical) via a communication link. Finally, upon selection of a Protocol active icon is made, a "Trash" icon becomes active allowing the selected Protocol to be deleted (a delete confirmation may be imposed).

Case Manager Step 42

Figures 7B, 8A:
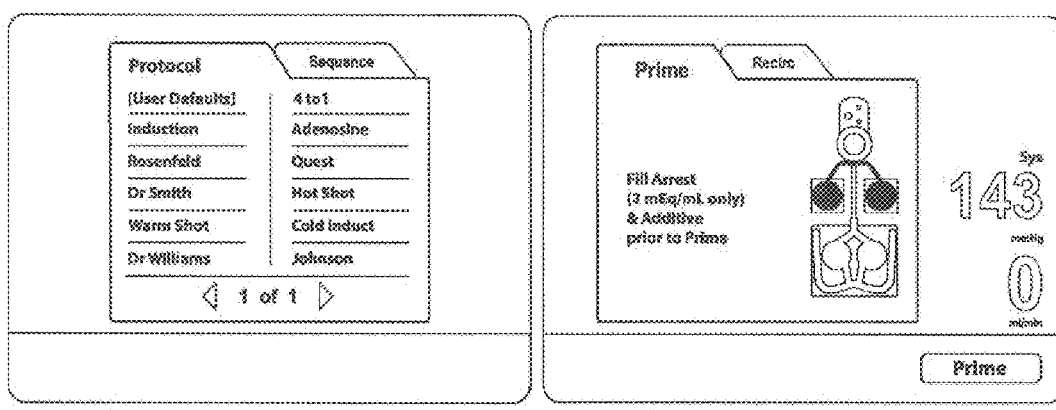
Figure 8I:
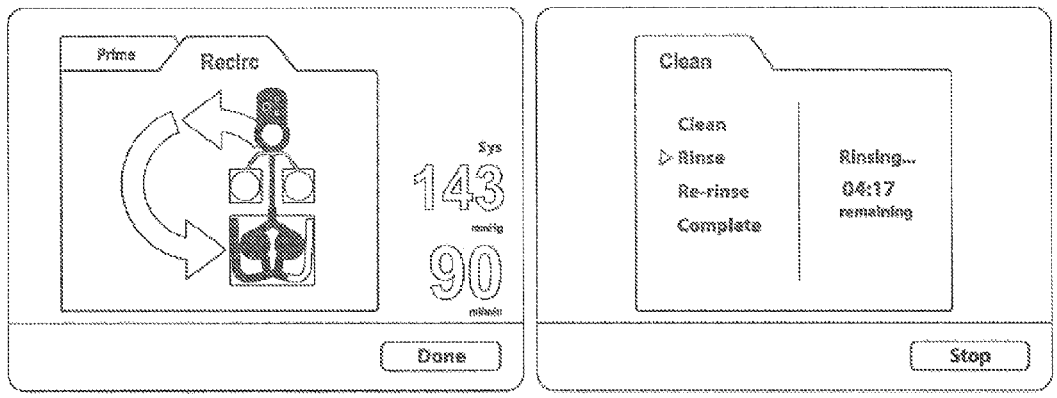
Figures 7, 9, 10A:
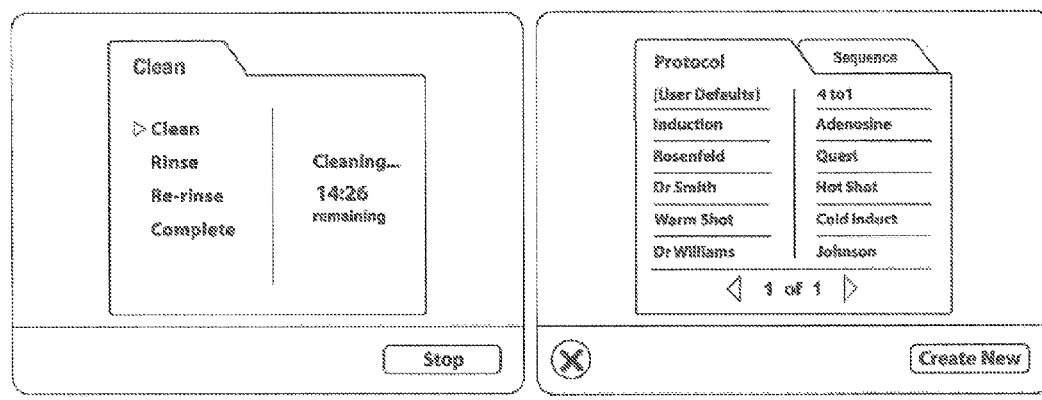
Figures 12, 13, 14, 15, 16:
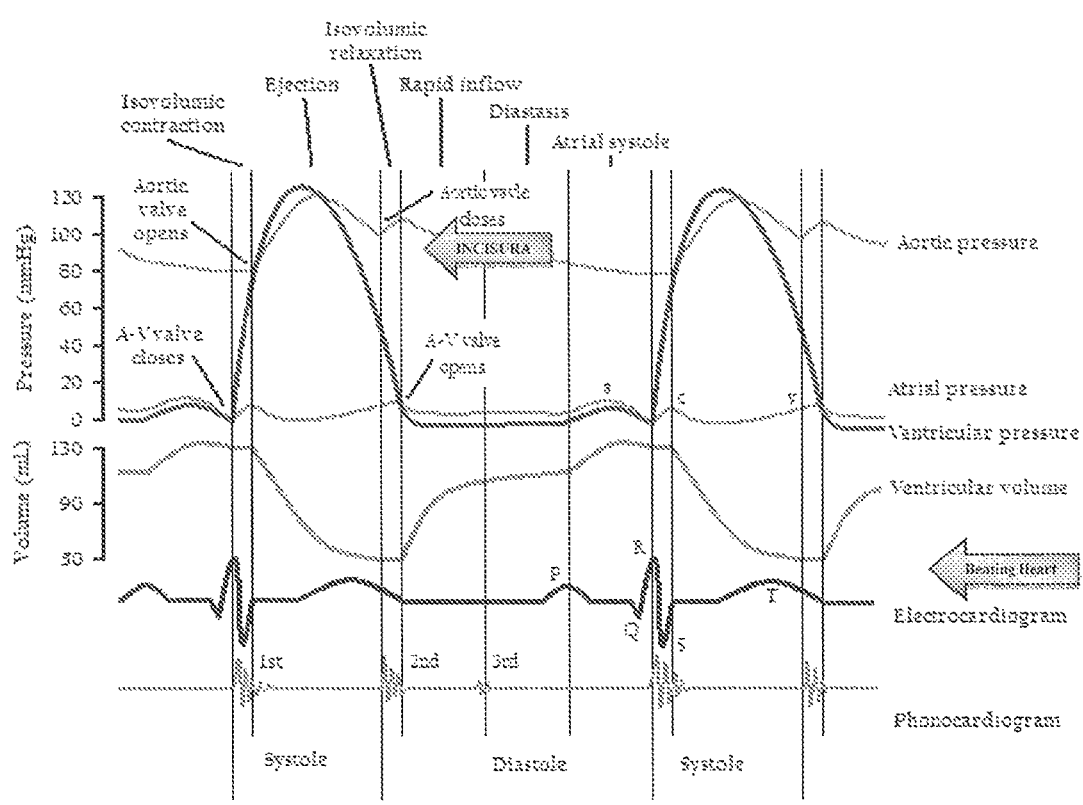

As shown in FIGS. 10A and 10B, selection of the Case Manager active icon from the Select Screen (FIG. 6), presents a tabbed Case Manager screen listing the predefined Protocols under the Protocols tab (FIG. 10A) and the predefined Sequences under the Sequences tab (FIG. 10B) (similar to the New Case Setup screens shown in FIGS. 7B and 7C). However, unlike the New Case Setup screens of FIGS. 7B and 7C, the Case Manager screens each include a Create New active icon and a Delete (i.e., X) active icon, allowing new Protocols and Sequences to be created and existing Protocols and Sequences to be deleted.

Referring to FIGS. 11-1 through 11-12, the User Default screens preferably originate from factory-predefined default parameters such as those set forth in the above table, that are then modified (i.e., "tweaked") as desired, and then saved to become the "User Default" Protocol (which may then be restored to the original factory-defaults).

The navigation of the User Default screens (and each of the Protocol screens of FIG. 12 described below) is similar in operation to the New Case Setup screens of FIGS. 7-1—-7-8A described above. More specifically, each default parameter may be tweaked within the factory-preset ranges or options set forth in the above table. For modification of numerical parameters, the parameter is highlighted by selecting whereupon a slider bar is presented in the lower portion of the screen showing the current numerical value of the parameter. As the perfusionist slides the slider left to decrease or right to increase the numerical value as desired, the value displayed changes accordingly. The length of travel of the slider is limited to the factory default ranges set forth in the above table. For modification of parameters having two or more modes, the parameter is selected whereupon a "fly-out" list of options is displayed allowing the perfusionist to select one.

Once defined and saved, the User Default protocol may be selected during New Case Setup or used as the starting point for defining new protocols.

Protocols

As shown in the screen of FIG. 12-1, upon selecting the Create New active icon from the Protocol screen (FIG. 10A), a new protocol may be created based upon the Current Case Parameters, the User Default protocol, an Existing Protocol or the Factory Default protocol. (if an Existing Protocol is selected, the Existing Protocols are displayed in a list in a screen (see FIG. 10A) allowing one of them to be selected).

Upon selection of the desired base for the new protocol, the parameters thereof are displayed in various screens allowing them to the reviewed and modified as desired (see for example FIGS. 12-2 through 12-14 based upon the Existing Induction 71808 protocol) using navigation similar to that described above in connection with navigation of the User Default protocol and New Case Setup. As shown in FIG. 12-15, when the parameters are changed as desired and the Save active icon is selected, an on-screen keyboard is presented allowing the new protocol to be named (e.g., copying the Existing Induction 71808 protocol as modified as new protocol called Dr. Jo). The name may comprise any desired phrase that describes the new protocol (e.g., Induction 71808), any desired name (e.g., the Doctor's name who created the new protocol) or any other identifier as may be desired.

Sequences

In addition to creating each surgeon's cardioplegia protocol preferences for each phase of the cardiac surgery such as induction, maintenance, and re-warm phases as described above, a sequence of such protocols may be created. More particularly, as shown in the screens of FIG. 13-1 through 13-7, upon selecting the Create New active icon from the Sequences screen (FIG. 10B), a new Sequence may be created by combining the User Default Protocol and/or Existing Protocols in the desired sequence. "Pauses" may be inserted between Protocols as desired to cause the sequencing to pause and not resume until some other action is taken or occurs.

For example, referring to FIG. 13-1 showing the creation of a new Sequence to be named "Lake MedCtr 101", one of the existing protocols listed to the left may be selected (e.g., "4 to 1") (FIG. 12-2) and then the Add active icon is selected to copy that selected protocol into the sequence listing on the right (FIG. 13-3) (conversely, the Del action icon may be selected to remove the protocol). The Pause active icon may be selected (FIG. 13-4) to insert a pause into the sequence being created (FIG. 13-5). Additional protocols (e.g., "Adenosine", "Cool shot" and Vent al 2") may be sequentially added to the sequence. It is noted that Up and Down active icons are provided to move a protocol up or down in the sequence to thereby conveniently reorder the sequence as desired. Once the sequence is complete, selection of the Save active icon displays an on-screen keyboard (FIG. 13-7) allowing the Sequence to be named as desired and saved.

Home Screen Step 60

Figures 1, 13:
Figures 3, 13:
Figures 2, 13:
Figures 4, 13:
Figures 5, 7, 13:
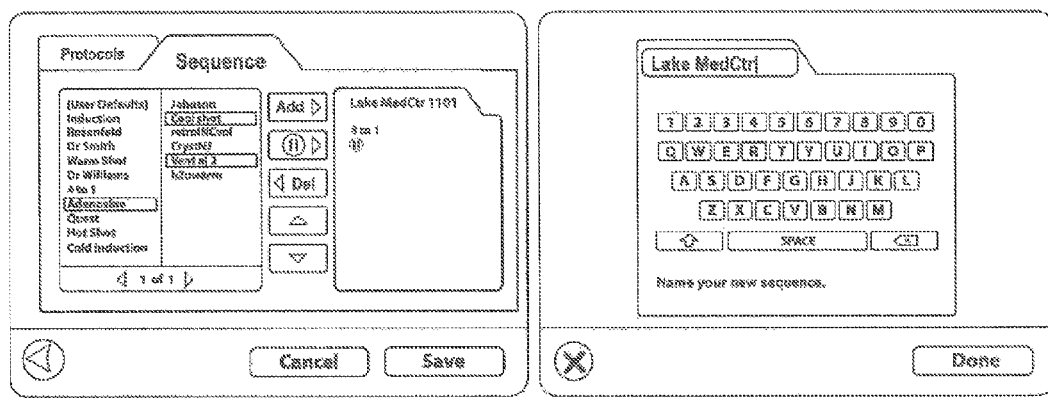
Figures 6, 13, 14A:
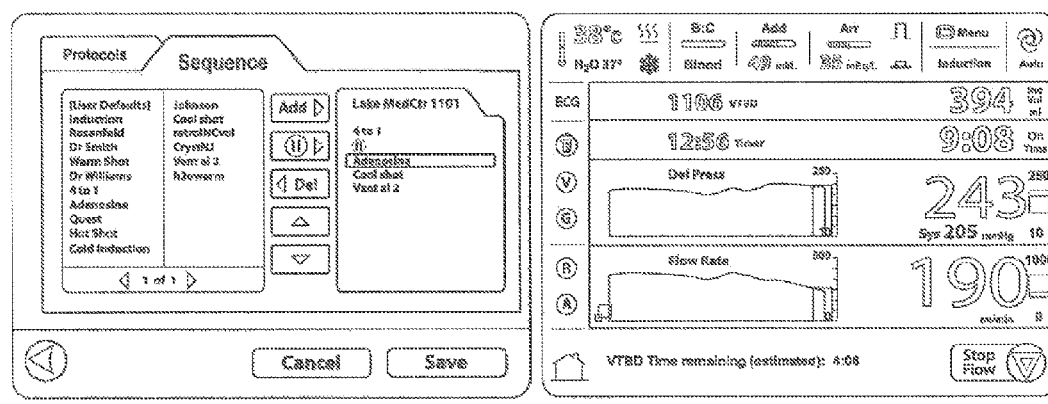

The Home Screen Step 60 allows the perfusionist to monitor and control the delivery of cardioplegia to the patient during surgery. Several views are provided: Chart View (FIG. 14A), Zoom View During Auto Mode (FIG. 14B), ECG View (FIG. 14C), Cyclic with Slider Bar View (FIG. 14D), Protocol View (FIG. 14E) and Sequencing View (FIG. 14F).

More specifically, in the Chart View Home Screen (FIG. 14A), the Flow Rate Real-time Chart shows a dynamic blue ribbon graph of the historical flow rate values with a one minute history that updates every half second. The ribbon graph shows simulated movement when the flow rate is greater than 0 and appears stopped and grayed when flow rate is 0. Preferably, the Flow Rate Chart's flow axis maximum is 200 ml/min in Low Volume flow mode, and 500 ml/min in Cyclic Flow Mode and in Normal Flow mode. If the perfusionist sets the flow rate above 500 ml/min while in Normal flow mode, the flow axis maximum is automatically changed to 1000 ml/min and the color of the ribbon display changes to a different shade of blue. When flow rate stays below 400 ml/min for a contiguous 1 minute interval, the flow axis maximum dynamically changes back to 500 ml/min. During Auto and Auto Flow modes (described below), the upper and lower flow limits are calculated and displayed. The blue ribbon graph shows one minute historical flow rate information and the flow rate on the Y axis dynamically auto scales according to the flow limits. The Flow Rate Chart is used to indicate the current flow mode when in either Low Vol mode or Cyclic Flow mode by showing the appropriate icon.

The Delivery Pressure Chart shows a dynamic green ribbon graph of the historical delivery pressure values with a one minute history which updates eight times every second. The pressure values are filtered through a trailing 20-point moving average filter prior to being displayed except in Cyclic Flow mode. The graph dynamically auto scales according to the pressure limits.

Figure 14B:
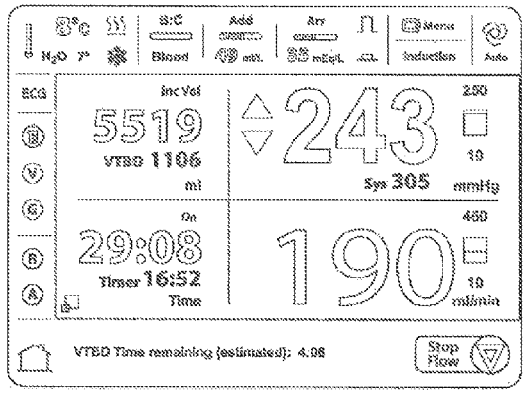

Referring now to FIG. 14B, the Zoom View Home Screen shows the Flow, Pressure, Time and Volume numerical displays enlarged. The ECG Home Screen (FIG. 14C) shows the ECG chart window whereas the Cyclic Home Screen (FIG. 14D) shows the Cyclic settings window in lieu of the ECG chart. The Protocol View Home Screen (FIG. 14E) shows the protocol being run. The Sequencing View Home Screen (FIG. 14F) shows the playing of the predefined Sequence.

The Flow Rate display includes a dynamic vertical flow bar shown to the right of the numeric flow display with the flow limits (e.g., 0-1000 ml/min) displayed. The bar dynamically represents the current flow rate value with respect to the flow limits. The lower flow limit is 0 in all modes except in Auto and Autoflow Modes where it is 10. The upper flow limit is 1000 in Normal Flow mode, 500 in Cyclic Flow mode and 200 in Low Vol Flow mode except in Auto and Autoflow modes. These flow limits may be adjustable in Auto and Autoflow Modes only. An Override active icon is displayed only in the Auto and Autoflow modes, the upper and lower flow limits being adjustable. Selecting the limit highlights the parameter and shows the slider bar allowing the adjustment. When the Override active icon is selected, the flow limits are overridden by graying out the upper and lower limits, placement of a red 'X' icon over the middle of the flow bar, and sending an override-mode message to the MPS Console 14.

As shown in FIGS. 15-1 and 15-2, during flow mode when flow is stopped, Single and Double Flow active icons are presented to allow selection of select Single or Double delivery line types. These active icons are paired i.e. either one but never both are selectable at the same time. The active icons appropriately change to indicate which selection is active. The selected delivery line type is saved in memory and messaged to the MPS Console 14.

When either Single or Double active icon is selected and Vent active icon is not activated, Simul is active. Selecting Simul (when active) shows the active icon selected and also both the Ante and Retro icons selected. The delivery direction may change by touching either Ante or Retro.

The Low Vol active icon is active if the current flow rate is 0 ml/min. When flowing in the Low Vol flow mode at the max flow rate of 200 ml/min and rotation of the Flow Knob is detected beyond the upper flow limit, an alarm is reported. This alarm gives the perfusionist the option to change the Flow Mode to Normal.

The Cyclic Once and Always Cyclic active icons are active if the current flow rate is between 10 and 500 ml/min, and if the current Flow Mode is Normal, and if Auto & Vent Modes are not activated. The Cyclic Settings allow the perfusionist to set the Amplitude, Duty Cycle, and Frequency (which is then messaged to the MPS Console 14). The range for frequency is 50-90 beats/min, for amplitude 50% to 400%, and for Duty Cycle 10% to 50% (% of time spent in the 'ON' cycle flowing at the upper flow rate) as may be modified by the following rules:

1. If the MPS is flowing at 100 ml/min, an amplitude of 100% means that when the MPS Console 14 is in the 'ON' cycle it will flow at 200 ml/min. The Flow Rates are calculated using the following formula:

upperFlowRate=flowRate*amplitude lowerFlowRate=((dutyCycle−amplitude)*flowRate)/(dutyCycle−1)

2. The max Flow Rate that is allowed in Cyclic mode is 500 ml/min. However the internally calculated upper flow rate is limited to 750 ml/min. If the calculated upper Flow Rate exceeds 750 ml/min, the Flow Rate is forced to 750 ml/min and the amplitude is recalculated using the below formula:

Amplitude=750/flowRate

3. If the calculated lower Flow Rate is less than 10 ml/min, the following formula is used to calculate the new amplitude:

Amplitude=dutyCycle−(flowRate*(dutyCycle−1)/flow rate)

The recalculated Amplitude replaces the perfusionist's setting and is displayed immediately. The Average Flow Rate is displayed when the upper pressure limit is exceeded.

Referring to the Chart View and Zoom View of the Home Screen (FIGS. 14A and 14B), the Delivery Pressure is displayed with a range of −99 to 999 mmHg. The System Pressure is displayed below the Delivery Pressure in smaller text with a range of −99 to 999 mmHg (only if the pressure sensor source selection for the delivery route is External). The displayed value is preceded by the 'Sys' label. The displayed pressure values flashes if the value is negative. Upper and lower pressure limits are displayed. If they have been overridden, they are grayed out and made not adjustable. Selecting the limit highlights the parameter and shows the slider bar. The range, store names and messages associated with each pressure limit is listed in the following table:

| Route | Source | Upper Limit | Range (mmHg) | Lower Limit | Range (mmHg) |
| --- | --- | --- | --- | --- | --- |
| Antegrade | System | PD_ANTE_SYS_MAX | 1-500 | PD_ANTE_SYS_MIN | 0-lower {350, (UL-10)} |
| | External | PD_ANTE_PRESSURE_MAX | 1-250 | PD_ANTE_PRESSURE_MIN | 0-lower {200, (UL-10)} |
| Retrograde | System | PD_RETRO_SYS_MAX | 1-500 | PD_RETRO_SYS_MIN | 0-lower {350, (UL-10)} |
| | External | PD_RETRO_PRESSURE_MAX | 1-125 | PD_RETRO_PRESSURE_MIN | 0-lower {80, (UL-10)} |
| Graft | NA | PD_GRAFT_PRESSURE_MAX | 1-200 | PD_GRAFT_PRESSURE_MIN | 0-lower {190, (UL-10)} |

A dynamic vertical pressure bar with an override active icon is shown to the right of the Delivery Pressure. The bar dynamically represents the current delivery pressure value with respect to the pressure limits. When the override active icon is selected, the pressure limits may be overridden by graying out the upper and lower limits.

Figure 14D:
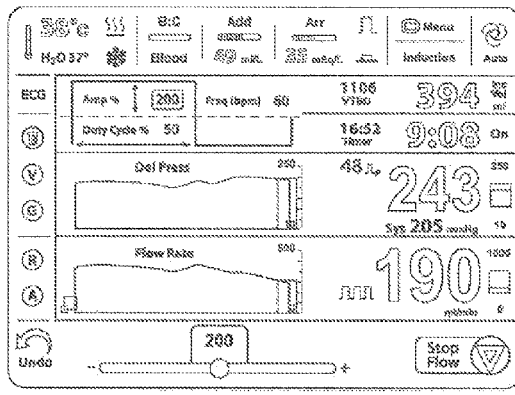
Figure 14C:
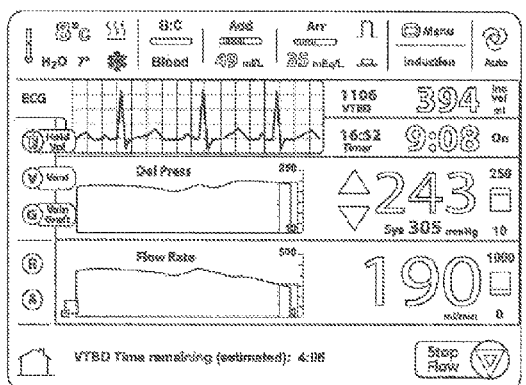

When flowing in the Cyclic flow mode, the pulse pressure (e.g., 48) is displayed in mmHg beside a pulse pressure icon (see FIG. 14D.)

Figures 10, 15:
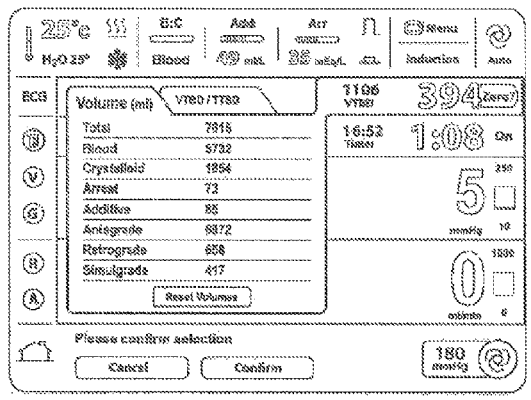
Figures 1, 15:
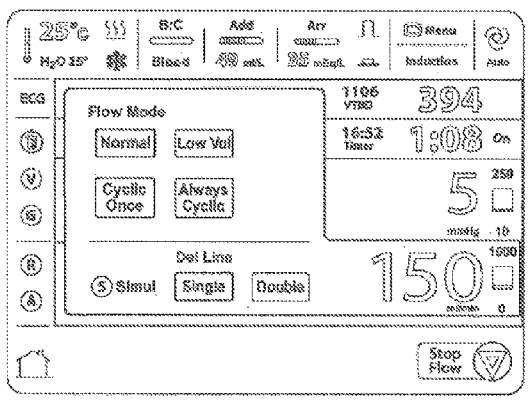
Figures 11, 15:
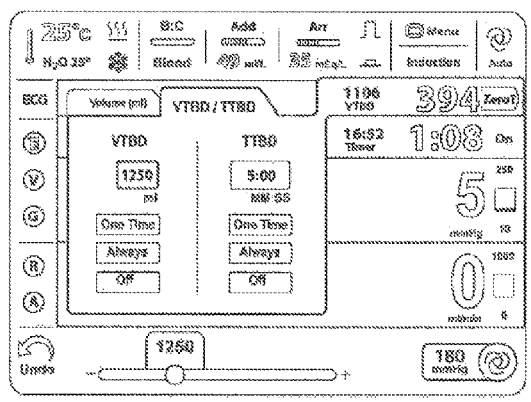
Figures 12, 15:
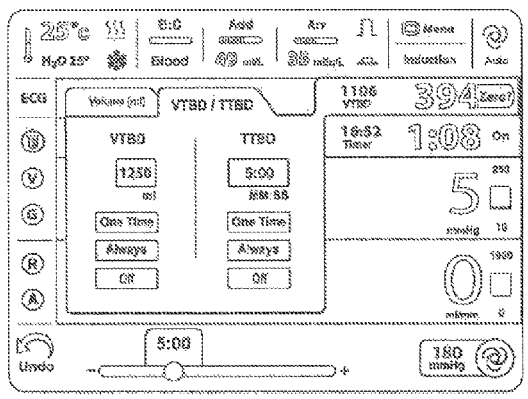
Figures 14, 15:
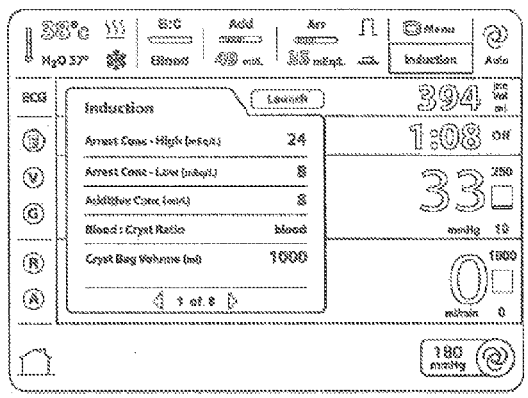
Figures 13, 15:
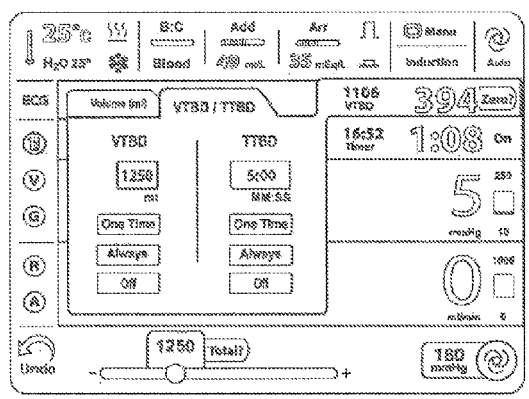
Figure 15:
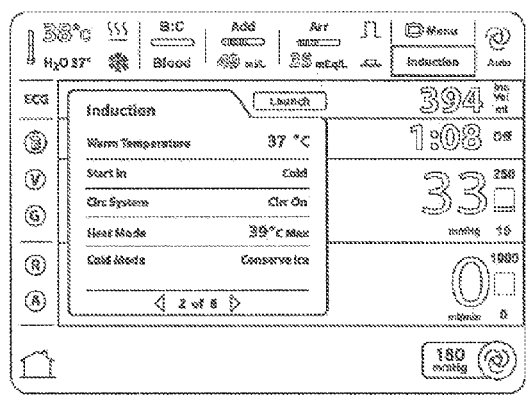
Figures 15, 16:
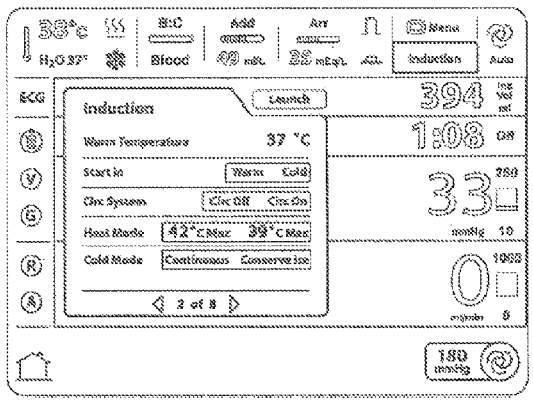
Figures 15, 16, 17, 18:
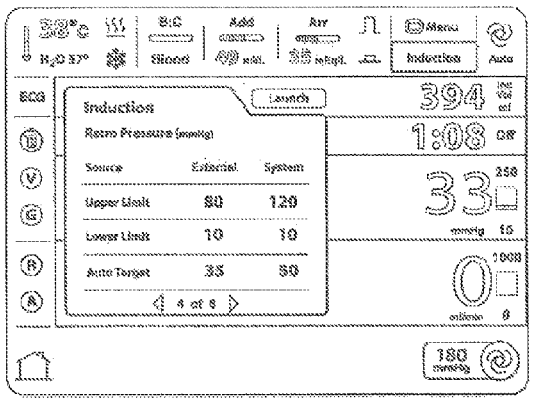
Figures 15, 16, 17:
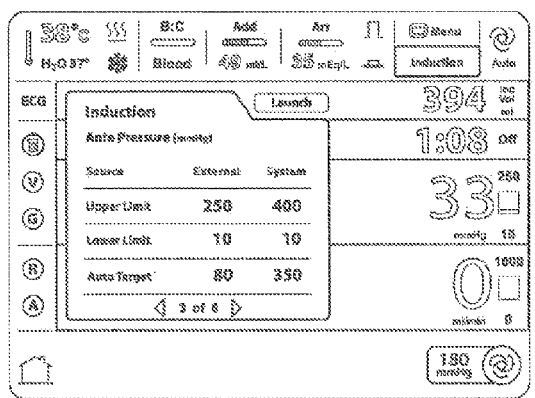
Figures 15, 16, 17, 18, 19:
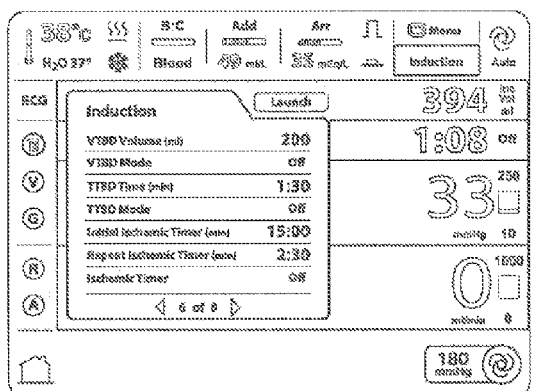
Figures 2, 15:
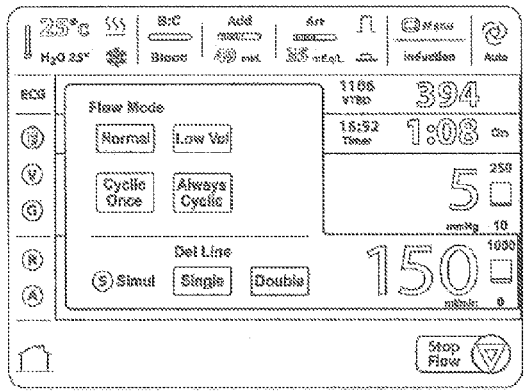
Figures 15, 16, 17, 18, 19, 20, 21:
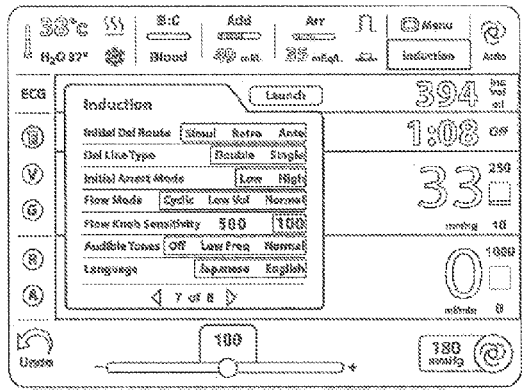
Figures 15, 16, 17, 18, 19, 20:
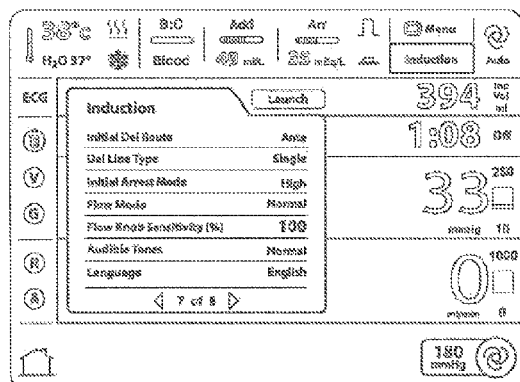
Figures 15, 16, 17, 18, 19, 20, 21, 22:
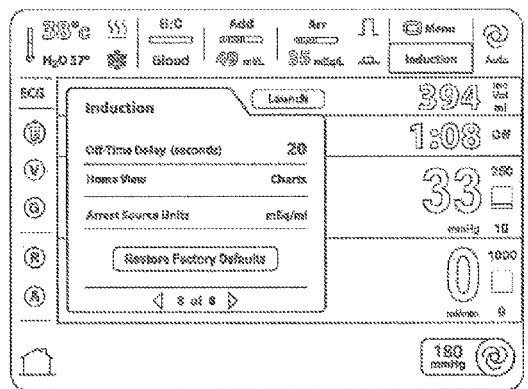
Figures 15, 16, 17, 18, 19, 20, 21, 22, 23, 24, 24A:
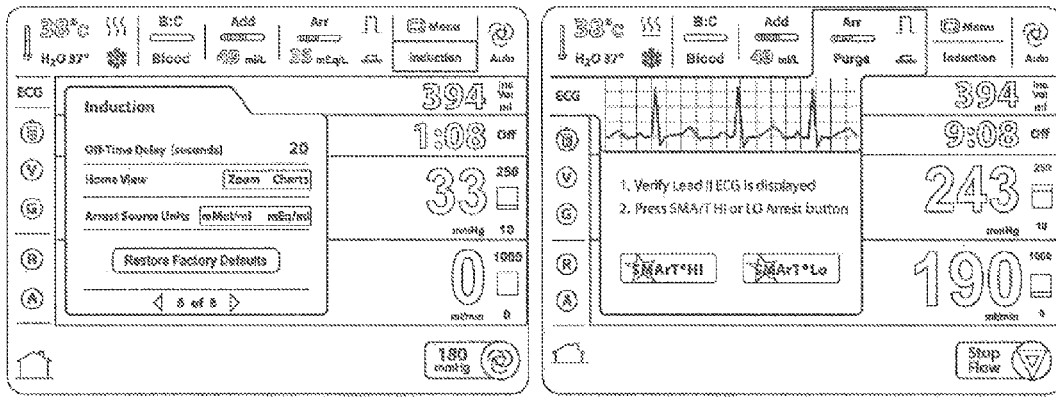
Figures 15, 16, 17, 18, 19, 20, 21, 22, 23, 24, 25:
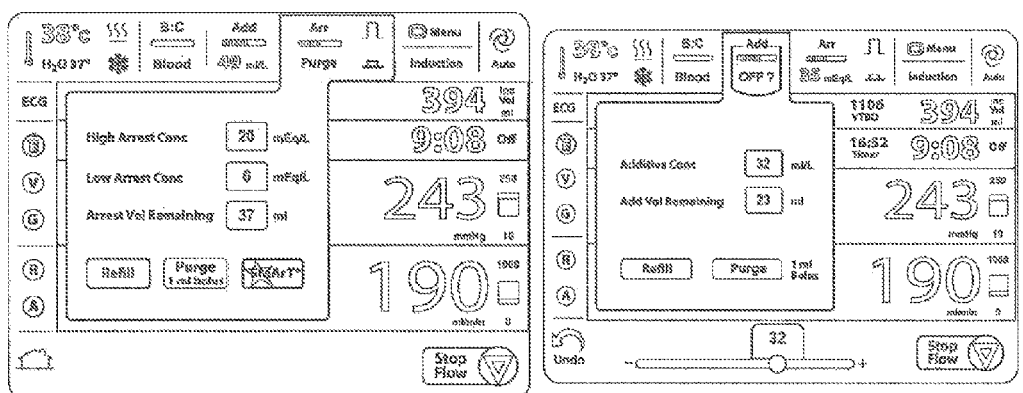
Figures 15, 16, 17, 18, 19, 20, 21, 22, 23, 24, 25, 26, 27, 28, 29, 30, 31, 32, 33:
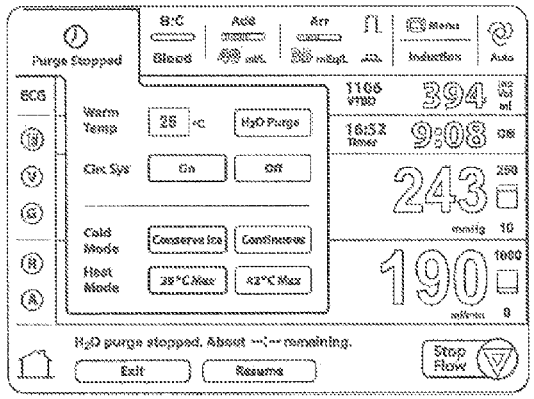
Figures 15, 16, 17, 18, 19, 20, 21, 22, 23, 24, 25, 26, 27, 28, 29, 30, 31, 32, 33, 34, 34B:
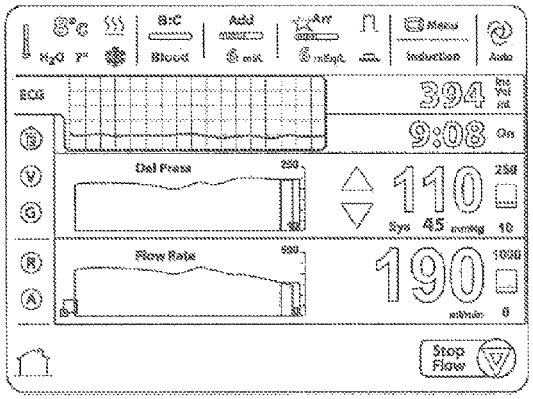
Figures 15, 16, 17, 18, 19, 20, 21, 22, 23, 24, 25, 26, 27, 28, 29, 30, 31, 32, 33, 34:
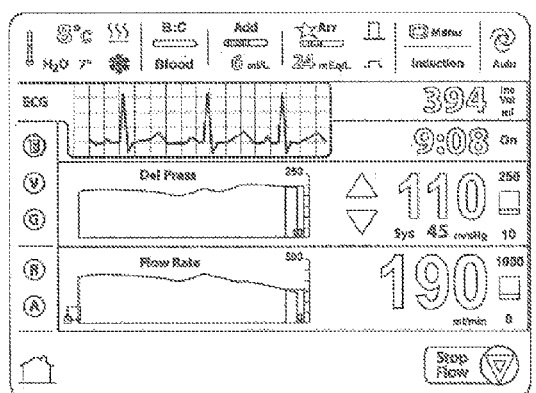
Figures 15, 16, 17, 18, 19, 20, 21, 22, 23, 24, 25, 26, 27, 28, 29, 30, 31, 32, 33, 34, 35:
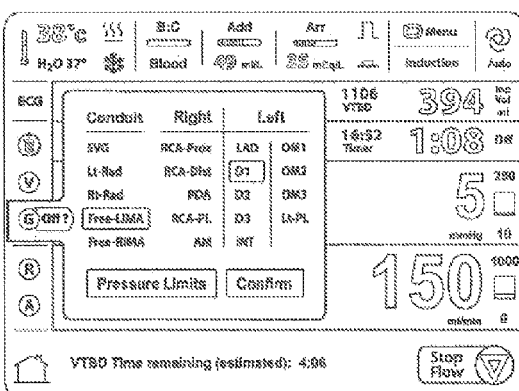
Figures 15, 16, 17, 18, 19, 20, 21, 22, 23, 24, 25, 26, 27, 28, 29, 30, 31, 32, 33, 34, 35, 36:
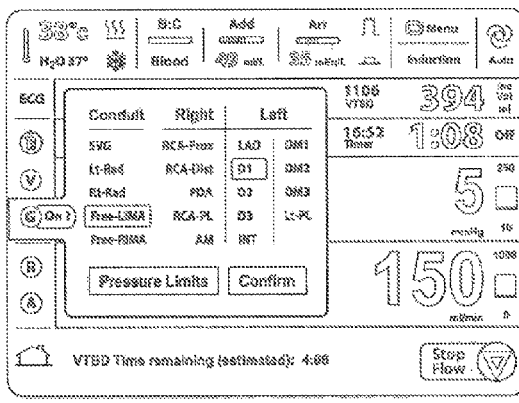
Figures 15, 16, 17, 18, 19, 20, 21, 22, 23, 24, 25, 26, 27, 28, 29, 30, 31, 32, 33, 34, 35, 36, 37, 38:
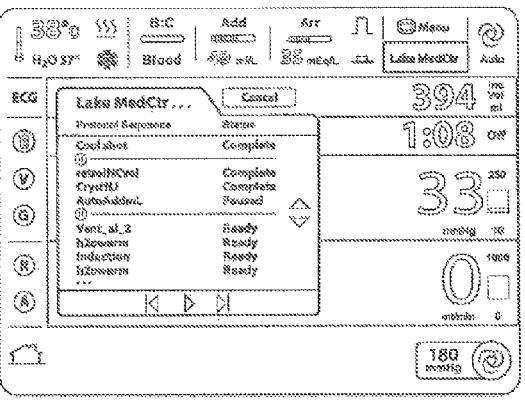
Figures 15, 16, 17, 18, 19, 20, 21, 22, 23, 24, 25, 26, 27, 28, 29, 30, 31, 32, 33, 34, 35, 36, 37:
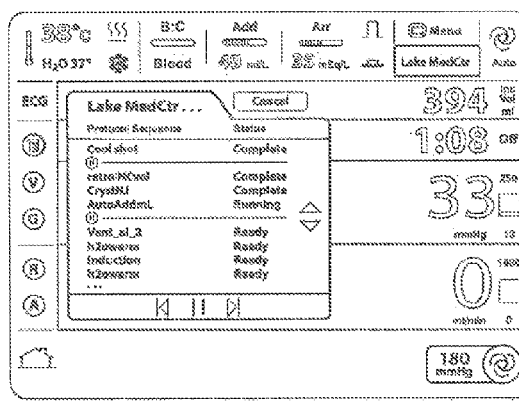
Figures 4A, 15:
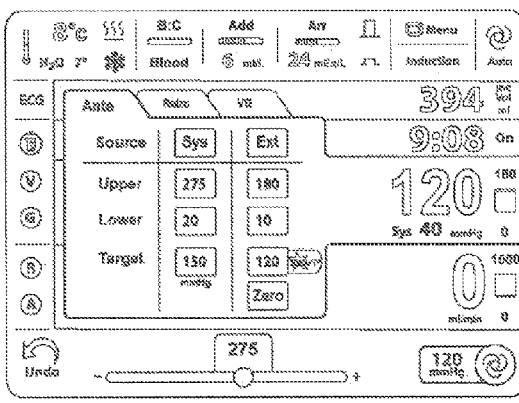
Figures 4B, 4D, 15:
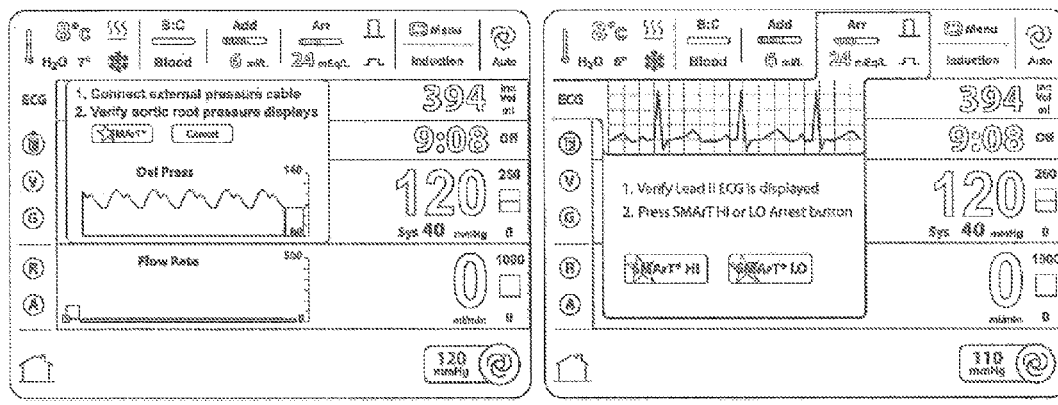
Figures 4C, 5, 15:
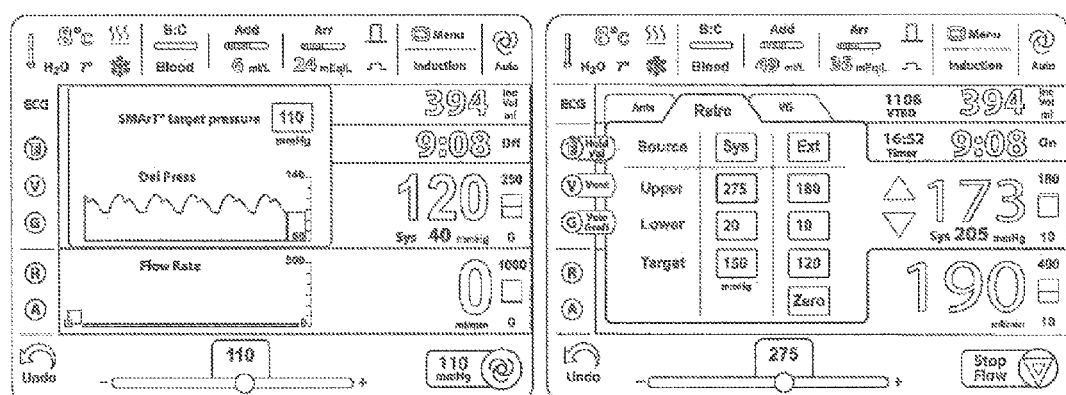
Figures 6, 15:
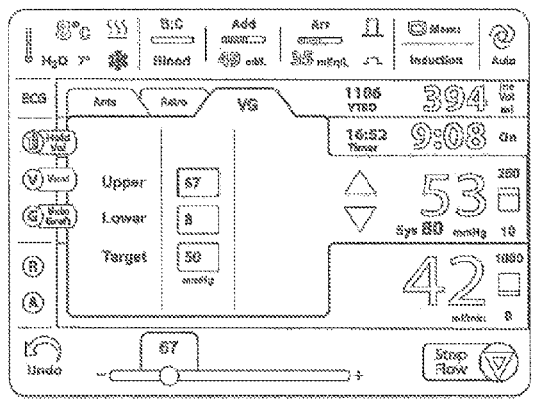
Figures 8, 15:
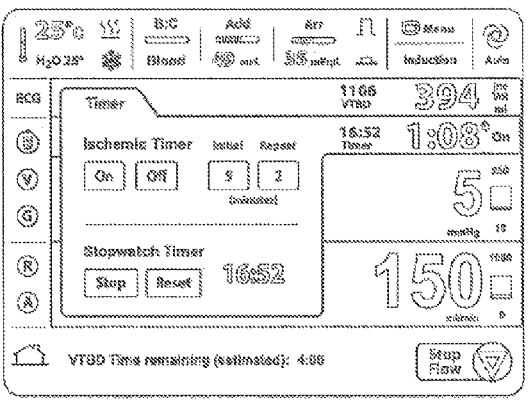
Figures 7, 15:
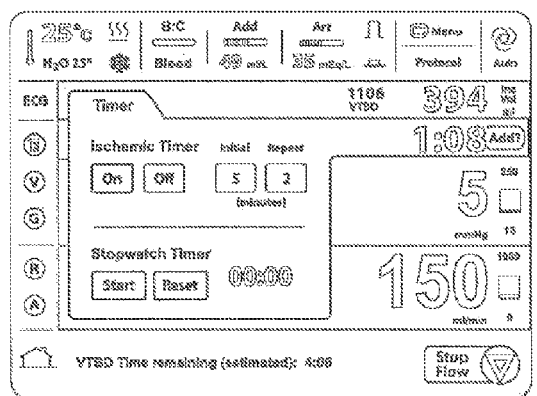
Figures 9, 15:
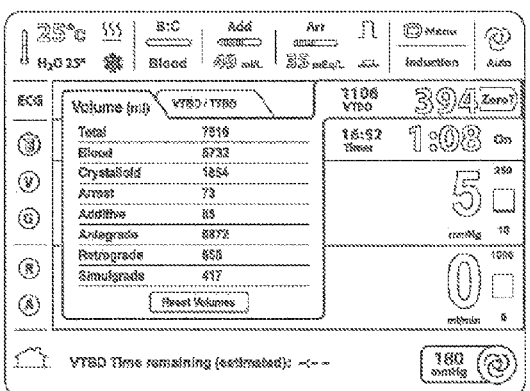
Figure 16:
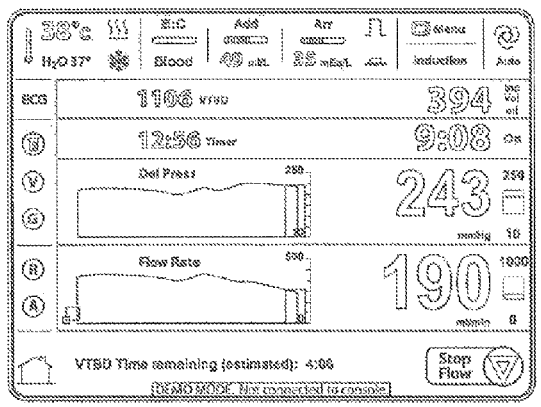
Figures 2, 17:
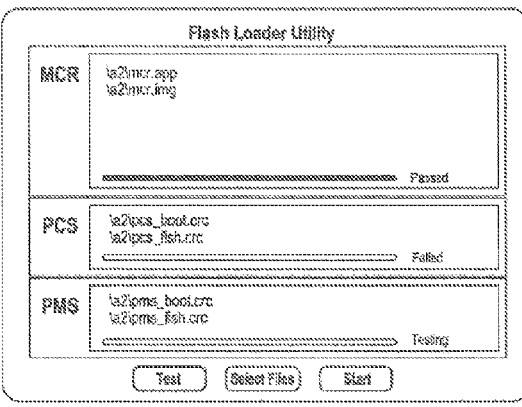
Figures 1, 17:
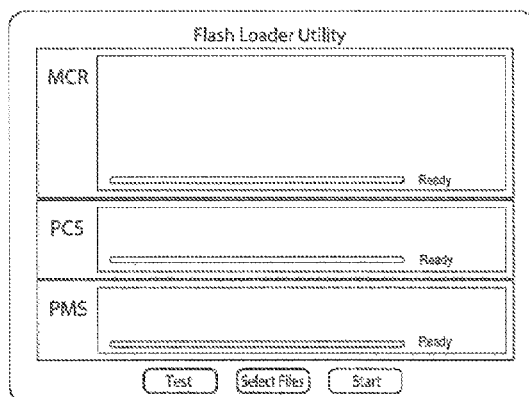
Figures 3, 17:
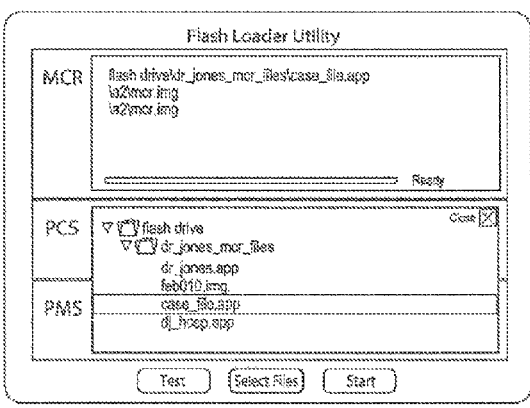
Figures 4, 17:
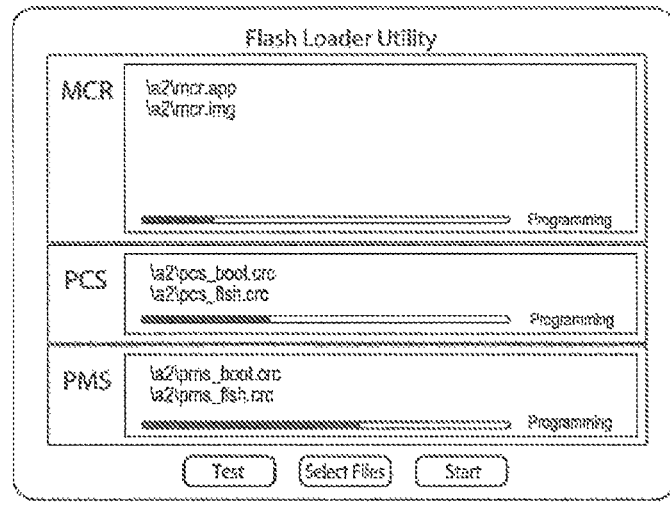
Figures 5, 17:
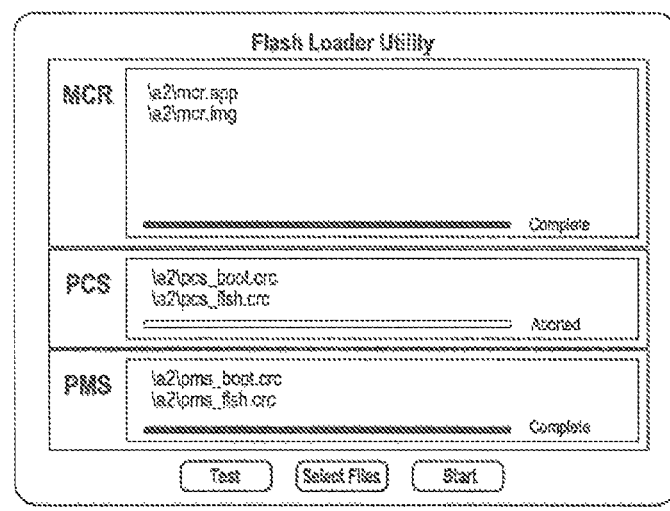

As shown in FIG. 15-4A, when selecting the pressure screen and the Override active icon is pressed, Antegrade, Retrograde and Vein Graft pressures are displayed as tabbed windows. The tabs are active and transition to the appropriate screen when selected. The upper pressure limit display corresponding to the selected delivery mode and pressure source selections are highlighted and ready to be set by default.

The Upper Antegrade System Pressure Limit range is 1-500 mmHg in increments of 1. The Lower Antegrade System Pressure Limit range is 0-350 mmHg or 0-Upper Antegrade System Pressure Limit minus 10 (whichever is lower) in increments of 1. The Antegrade System Target Pressure range is 10-500 mmHg in increments of 1. The Upper Antegrade External Pressure Limit range is 1-250 mmHg in increments of 1. The Lower Antegrade External Pressure Limit range is 0-200 mmHg or 0-Upper Ante External Pressure Limit minus 10 (whichever is lower) in increments of 1. The Antegrade External Target Pressure range is 10-250 mmHg in increments of 1. The Zero active icon is used to Zero the Antegrade External Pressure sensor. Because the External transducer cannot be zeroed while flowing, the Ante Source has External and System presented as options that are valid only if flow is 0. System and External are mutually exclusive selections for antegrade pressure source.

As shown in FIG. 15-4A-D, while viewing under the Antegrade tabbed window, the perfusionist is provided the option of selecting a detector (hereinafter referred to as Safe Myocardial Arrest Technique or TM "SMArt") that detects the closure of the aortic valve.

By way of background, the coronary arteries provide blood and nutrients needed for the myocardium to perform the work of circulating oxygenated blood through the body. Back-flow during diastole (left-ventricular filling) and pressure closes the aortic valve in situ directing flow down the coronaries. Consequently, if the aortic valve is not closed quickly during cardioplegia induction, reduced or no flow of oxygen and nutrients goes through the coronary arteries. In this situation the myocardium continues to contract and uses energy which it will need when it resumes beating again at the end of surgery. The heart will be working against the high resistance of a crossclamped aorta. Working the heart muscle at the induction stage of open-heart surgery, without coronary artery perfusion to sustain it, is undesirable and creates an acidotic myocardial condition due to lack of oxygen. In addition, if the aortic valve is not closed quickly, large volumes of cardioplegia are sent directly into the left ventricle raising the patient's serum potassium concentration levels. If the serum potassium concentration goes high enough above normal, counter-measures (such as blood-filtering and giving intravenous medications) are employed to reduce it back to normal. Achieving aortic valve closure for cardioplegia surgery is therefore necessary to direct high-potassium carrying cardioplegia down the coronary arteries to induce arrest in on-pump open-heart surgery. In manually-operated prior art cardiolpegia, it is difficult to reliably increase cardioplegia flow quickly to a safe yet effective unknown aortic valve closure pressure.

Referring to the diagram of FIG. 12-16, SMArT determines cardioplegia volume by measuring a patient's ascending aorta (AA) pressure representative of the cardioplegia delivery pressure and monitoring an electrocardiogram (ECG). The cardioplegia delivery pressure and volume is quantified and used to determine the appropriate induction dose pressures, volumes, and flow to then be delivered automatically (under direct supervision of the profusionist) to achieve aortic closure, thereby removing any guesswork or trial-and-error.

More specifically, the pressure at the aortic incisura of the ascending aorta (AA) is used as input into an Auto Flow target pressure parameter. Auto Flow then delivers cardioplegia in a quick and automatic way to this target pressure. This forces the cardioplegia to flow down the coronary arteries, and arrest the heart. The cardioplegia target pressure is then automatically maintained throughout the induction stage of the surgery to ensure the aortic valve remains closed. Target pressure can be adjusted manually during this delivery phase if desired without interrupting the steadiness of delivery pressure.

After cardiac arrest, SMArT continues to monitor the ECG for any heart activity. As some heart activity becomes evident from monitoring the ECG, SMArT automatically increases Low Arrest Concentration. Conversley, the lack of any heart activity over a period of time causes SMArT to automatically lower the Low Arrest Concentration. The amount of increase/decrease may be dynamically computed based upon the frequency and amplitude of the heart activity.

Thus it should be appreciated that delivered cardioplegia volume and duration is monitored automatically. Once the ECG is triggerd indicating heart arrest, the duration and volume of cardioplegia required for cardiac arrest is recorded. If existing protocols require it, a bolus (i.e., VTTB as part of the induction dose), additional volume can be given automatically. Cardioplegia is automatically stopped after all preset cardioplegia induction volumes or durations are delivered. Cardioplegia may also be stopped manually via the Flow Knob.

The historical delivery of cardioplegia volume and duration High Volume and Low Volume may be used for computing a suggested baseline target pressure (and then accepted by the perfusionist).

In summary, the following is a preferred method for SMArT:
1. Ascending aorta (AA) pressure is monitored.
2. The incisura on the AA pressure curve is detected.
3. The pressure obtained in step 2 is then used as the Target Pressure of the Auto Flow function.
4. The Volume-to-be-Delivered is set, indicating either "total induction dose" volume or "after induced arrest" volume.
5. At the time for delivery, Auto Flow is initiated and the target pressure is automatically reached, and then held constant. The constant delivery pressure can be incrementally adjusted higher or lower.
6. The electrocardiogram (ECG) waveform is monitored.
7. Delivery of cardioplegia continues until the ECG waveform flattens indicating cardiac arrest. Delivery time and volume of cardioplegia are recorded.
8. Volume To Be Delivered "after induced arrest" is triggered to begin decrementing its count down as cardioplegia delivery continues. While still in the induction phase, deliver a liter.
9. Cardioplegia delivery stops once the Volume To Be Delivered (either "total induction dose" or "after induced arrest") has been delivered. The perfusionist may manually stop cardioplegia delivery at any time.

It should be appreciated that steps 4, 8, and 9 provide fully automatic cardioplegia delivery but may optionally be omitted if desired.

Representative uses of using SMArT include:
1. ECG as an indication for Arrest Agent concentration:
  a. Arrest dose, Cold temperature, Intermittent delivery
    i. High KCl (potassium chloride) is delivered to stop the heart (as indicated by a quiescent ECG),
    ii. Once quiescence is indicated, the KCL is lowered to a "maintenance" concentration for the remaining arrest dose (the Safe Myocardial Arrest Technique, SMArT, would monitor the ECG and change the KCL concentration from the high concentration to a low concentration).
    iii. In addition to the ECG as an indicator, a myocardial temperature probe may be used to insure the heart is protected by chilling the muscle cells which lowers the cell metabolism.

b. Maintenance dose, Warm or Tepid Temperature, Continuous delivery
  i. The myocardium is more active when it is warm. KCL and Additives (i.e. Magnesium) are needed continuously throughout the maintenance dose. Adjusting the concentration, higher if the ECG indicates activity and lower to prevent a rise in blood gas KCL, is critical to protect the heart during the case.
2. Aortic Root Pressure Waveform As An Indication Of Rate Of Delivery And Target Pressure For Arresting The Myocardium Ensuring That The Aortic Root Pressure And Retrograde Flow Is Sufficient To Close The Aortic Valve.
  a. The aortic valve contains three semilunar cusps separated by sinuses. Retrograde flow fills these sinuses, much like a parachute, to extend them into a position where the cusps touch and close off further retrograde flow into the left ventricle. Blood flow instead enters the ostia of the coronary arteries, which are located near the closed valve, and since the myocardium is in diastole and relaxed, blood flow is able to proceed through the coronaries to nourish the heart muscle.
  b. Insufficient antegrade cardioplegia delivery pressure may simply fill the left ventricle with KCL (i.e., not closing the cusps) and thereby resulting in the heart not arresting. Hence, both the rate of flow and pressure are critical to closing the "parachutes" of the sinuses and provide a quick arrest with minimum possibilities for deleterious effects. It is noted that the deleterious effects of a slow arrest may include (1) high blood potassium requiring blood filtration to enable the heart to restart, (2) too much ATP expenditure due to the work of the myocardium beating against a cross-clamped aorta (this energy expenditure results in an unnecessary strain on the already weak heart muscle and is unnecessarily consumed when it will be subsequently needed for restarting the heart and (3) little blood (oxygen and nutrients) flowing to the heart when the aortic valve is open generating a hypoxic condition.

As shown in FIG. 15-6, the perfusionist may select the Vein Graft tab to select the Vein Graft pressure. The Set Vein Graft Upper Pressure Limit active icon range is preferably 1-200 mmHg in increments of 1. The Set Vein Graft Lower Pressure Limit active icon range is preferably 0-Upper Vein Graft Pressure Limit minus 10 in increments of 1. The Set Vein Graft Target Pressure active icon range is preferably 10-Upper Vein Graft Pressure Limit minus 10 in increments of 1.

The Time display displays either 'On' Time or 'Off' Time. When the Set flow rate is greater than 0, 'On' Time is displayed. When flow is stopped the On Time halts. If flow remains stopped for a period greater than a programmable 'Off Time Delay', 'Off' Time displays and starts incrementing from 'Off Time Delay' seconds. If flow is resumed within 'Off Time Delay', it is considered part of the same 'On' time and the On timer begins incrementing again from that time-point forward as if uninterrupted.

As shown in FIG. 15-7, selecting the Off Time display causes an "Add" tab to appear for three seconds and transition to the Timer screen simultaneously. If the tab is selected within the 3 seconds the following occurs: (1) the previous On Time and the previous Off time is added to the current Off Time and the total Off Time is displayed immediately, (2) the associated 'On time' flow & pressure Dose data is deleted from the Dose record and then (3) the view transitions to Home. If the tab is not selected within 3 seconds, the tab fades away and the Time screen of FIG. 15-8 is presented.

Note that flowing in Vent, Recirc and/or Hold Vol modes, is not considered On Time. Instead the Off timer is incremented and displayed. Since a Dose is defined by Off Time, a dose shall also be terminated when either one of these modes is activated.

The Stopwatch Timer value is displayed beside the On or Off Timer if the value >0. The screen layout may adjust when a Flex Screen, ECG or Cyclic parameters screen is displayed. The Stopwatch Timer counts up every second when the timer is started and halts when the timer is stopped.

The Ischemic Timer enabled icon is displayed next to the timer if it is activated. The Set Ischemic Timer active icon allows the perfusionist to turn the Ischemic Timer On or Off, and to set the Initial and Repeat Ischemic timer values. When Ischemic Timer is enabled, the Ischemic Timer icon is shown on the Run screen. The Initial and Repeat Timers have a range of 1 to 60 minutes in 1 minute intervals. When the Off Time equals the Initial Ischemic Timer value and thereafter at intervals equal to the Repeat Timer value, a visual indication is provided by flashing the Off Time label and timer value for 5 seconds. The ischemic timer audible tone shall also be sounded at this time. The Ischemic Timer may be used, for example, to assure that no more than about 10 minutes between grafts with the Repeat Timer functioning like a snooze alarm.

When Start is selected, the Stopwatch timer starts counting up every second from the current timer value up to a maximum of 99 minutes and 59 seconds. When Stop is selected, the timer halts. When Reset is selected, the timer is reset to 00:00. If the timer was counting at the time Reset was selected, it may continue counting up after resetting to 00:00.

As shown in FIGS. 15-9 & 10. the Incremental Volume tab displays the total cardioplegia volume (blood+crystalloid+arrest+additive) delivered during the current 'On' Time. The range is 0 to 99999 ml. When flow is stopped, the Incremental Volume display continues showing the total cardioplegia volume. If flow is resumed within 'Off Time Delay', the Incremental Volume counter continues counting from the previous value. If flow is resumed after a halt greater than 'Off Time Delay', the counter is reset to zero and starts counting again.

Selecting the Incremental Volume tab display causes a "Zero?" tab to appear for three seconds and then transitions to the Volume screen. If the tab is selected within the 3 seconds, the incremental volume is rest to 0 and then transitioned to Home. If the tab is not selected within 3 seconds, the tab fades away.

The Volume and VTBD/TTBD modes are tabbed windows that are always active. Total, Blood, Crystalloid, Arrest, Additive, Antegrade, Retrograde and Simulgrade delivered volume counters are tracked and dynamically displayed to the perfusionist. The Reset active icon resets all the volumes to 0 after an additional confirmation screen (see FIG. 15-10.)

Selecting the VTBD/TTBD tab transitions to the VTBD/TTBD screen (see FIGS. 15-11 through 15-13). The remaining VTBDvolume is displayed whenever the value is >0, and the mode is set to One Time or Always (its screen placement may adjust when Flex Screen, Zoom Screen, ECG screen or Cyclic parameters screen is displayed). The displayed remainingVTBDvolume is decremented as volume is being delivered. The flow automatically stops and a single beep sounds when the remainingVTBDvolume value reaches 0. If the mode had been set to One Time, it shall automatically be set to Off when the remainingVTBDvolume reaches 0. If mode had been set to Always, the remainingVTBDvolume display is reloaded when the remainingVTBDvolume value reaches 0 and flow is stopped. If the flow is stopped by the perfusionist prior to the remainingVTBDvolume reaching 0, the remainingVTBDvolume stops decrementing, and resumes when flow is reinitiated.

The estimated time remaining to deliver the remainingVTBDvolume, based on the current flow rate, is shown in the message window. This estimated time remaining is updated dynamically when the flow rate or volume is changed. The estimated time remaining shows null (i.e., "--:--") when flow is stopped. Any other message requiring use of the message window dismisses this message temporarily with the need to re-display when possible.

The remainingTTBDtime of the Time To Be Delivered (TTBD) is displayed whenever the value is >00:00 and its mode is set to One Time or Always (its screen placement may adjust when a Flex Screen, Zoom screen, ECG screen or Cyclic parameters screen is displayed). The displayed remainingTTBDtime decrements every second when flow >0. When flow is stopped the remainingTTBDtime halts. When remainingTTBDtime reaches 00:00, the flow is automatically be stopped, a single beep sounded, its value is set to 0 and messaged to the MPS Console 14 and, if TTBD mode is set to One Time, is automatically set to Off.

If TTBD mode is set to Always, when the remainingTTBDtime reaches 00:00 and flow is stopped, the remainingTTBDtime is reloaded with the TTBD Time. If the flow is stopped by the user prior to the remainingTTBDtime reaching 0, the remainingTTBDtime stops decrementing, and resumes when flow is reinitiated.

The VTBD display shows the PD VTBD Volume and not the remainingVTBDvolume. When selected, it allows the user to set the PD VTBD Volume to any value between 10 and 4000 ml in 10 ml increments.

The VTBD display is highlighted and ready to be set by default when this state is transitioned to and TTBD is not activated (TTBD Mode is set to Off).

One Time, Always, or Off is shown as selected and highlighted based on VTBD Mode.

If the remainingVTBDvolume is greater than zero when a new VTBD Volume is being set, the slider displays a unique side-tab labeled "Total?" (see FIG. 15-13). This active icon moves along the slider as the parameter is being set. Selecting the "Total" active icon sets remainingVTBDvolume by first subtracting what has previously been delivered from the newly set VTBD value. (i.e., New remainingVTBDvolume=New PD VTBD Volume−[Previous PD VTBD Volume−remainingVTBDvolume]).

If the new VTBD value (determined by the slider position) becomes less than the previously delivered VTBD volume (i.e. Previous PD VTBD VOLUME−remainingVTBDvolume), a dynamically changing value when flowing, the "Total" active icon is disabled and grayed out. Selecting any other valid active icon sets the PD VTBD VOLUME to the newly selected value.

The VTBD One Time active icon sets VTBD Mode to One Time. The remainingVTBDvolume is loaded with the VTBD Volume. The VTBD Always active icon sets the VTBD Mode to Always. The remainingVTBDvolume is loaded with the VTBD Volume. The VTBD Off active icon resets the remainingVTBDvolume to zero. This effectively cancels VTBD until it is activated again (by selecting either One Time or Always).

The TTBD display shows the TTBD Time and not the remainingTTBDtime. When selected, it allows the user to set the TTBD Time to any value between 1:00 and 15:00 in 30 second increments. The TTBD display is highlighted and ready to be set by default when this state is transitioned to and TTBD is activated (TTBD Mode is set to One Time, or Always). One Time, Always, or Off is shown as selected and highlighted based on TTBD Mode. When confirmed, the TTBD Time is set to the newly selected value.

The TTBD One Time active icon sets the TTBD Mode to One Time. The remainingTTBDtime is loaded with the TTBD Time. The TTBD Always active icon sets the TTBD Mode to Always. The remainingTTBDtime is loaded with the TTBD Time. The TTBD Off active icon resets the remainingTTBDtime to zero. This effectively cancels TTBD until it is activated again (by selecting either One Time or Always).

Only one (and at least one) of the six active icons is allowed to be selected at any given time. The exception is when both VTBD and TTBD are set to Off, both Off active icons are shown as highlighted.

Auto Mode and Auto Flow Mode

The Auto active icon is used to activate and cancel Auto Mode (see FIG. 14A-E). The Auto Mode is disabled anytime flow is zero, delivery pressure is less than 10 mmHg (unless already in Auto Mode), Vent Mode is activated, or Recirc Mode is activated. The icon appropriately changes to indicate that Auto Mode is activated. The status is saved in Auto Mode and messaged to the MPS Pump. Auto Mode is automatically cancelled if the flow rate is changed, completion of a VTBD or TTBD, a Protocol or Sequence is launched, or by an error condition that stops flow. If Auto Mode is activated while Cyclic is activated, Cyclic Mode is first cancelled and then Auto Mode is activated. If Auto Mode is activated when Always Cyclic is active, Cyclic Flow Mode is cancelled for this one instance only.

When Auto or Auto Flow Mode is activated, the Auto active icon appears to be spinning clockwise using animation. The Target Pressure Increment active icon and Decrement active icon are displayed and the Override active icon is displayed in the Flow Bar.

The Target Pressure is adjustable by selecting either the Increment or Decrement active icons. The Increment active icon increases the Target Pressure in 1 mmHg increments and the Decrement active icon decreases the Target Pressure in 1 mmHg decrements. Holding down either active icon changes the parameter at the rate of 2 mmHg per second (in 1 mmHg increments). Pressure adjustments are sent to the pump using the Set Target Pressure message. Target pressure adjustments made in this manner are temporary and do not change the previously-set Target pressure values.

During Auto or Auto Flow Mode, the upper and lower flow limits are displayed. In Auto Mode, the upper flow limit is twice the flow rate value at the time Auto Mode is activated. In Auto Flow mode the upper flow limit is 600 (Normal), or 200 (Low Volume). The lower flow limit is 10 mL/min in both modes. The flow limit values are saved and messaged to the MPS Console 14.

The flow limits are settable by the perfusionist. Selecting the Flow Limit value highlights the parameter and show the slider bar. If changed, the value is saved and messaged to the MPS Console 14. The range is 10 to 1000 (Normal), or 10 to 200 (Low Volume) in increments of 10 ml/min. The lower flow limit is 10 or more ml/min less than the upper limit.

Protocol/Sequencer

A Protocol active icon and a Sequence active icon are displayed showing the Protocol Name (e.g., Induction) (see FIGS. 14A-E) and Sequence Name (Lake Med Cir) (see FIG. 14F).

Selecting the Protocol active icon transitions to the Protocol Screen (see FIG. 14E) showing a listing of Protocols.

Selection of a desired Protocol allows the parameters pertaining to the protocol being run to be displayed (see FIGS. 15-14 through 15-23), with Name (e.g. Induction) of the selected Protocol being shown in the tab of the Protocol Screen. As described above in connection with Case Manager, any protocol parameter may be changed by selecting the parameter and then either using the slider bar to make the change or selecting the option from the expanded list of options. After a selection is made from the expanded list, the list collapses and the new selection is shown. Any changes made may be saved back to the same store it was read from without affecting the Case parameters (see bidirectional arrows in the flowchart of FIG. 5).

Selecting the 'Launch' active icon activates the Protocol. All the parameters in the displayed protocol list are made the current case parameters by writing them to memory and messaging them to the MPS Console 14. Upon Launching, the screen transitions to Home (FIG. 14).

Figure 14E:
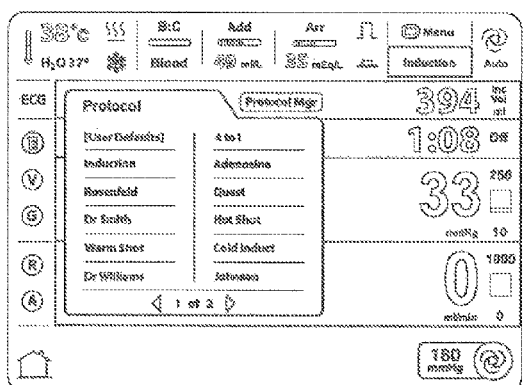
Figure 14F:
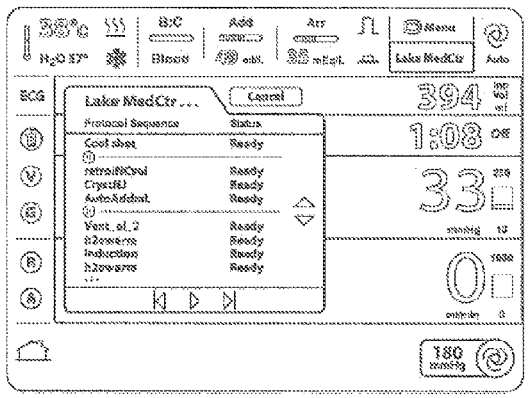

Likewise, selecting the Sequence active icon displays a Sequence Play screen in the Home View (see the Sequencer View FIG. 14E.) After launching, the Sequence Play screen and shows the Protocols of the Sequence being run and graphically shows them running in each successive screen (compare FIG. 14E with FIGS. 15-37 and 15-38). More particularly, the Sequence Name is shown in the tab of the Sequence Play screens. The Sequence Play Screen further includes a Play Bar comprising a Play/Pause active icon (Play is ▶ and Pause is ‖), Next Protocol active icon ▶| and a Previous Protocol active icon |◀. With regard to the Play/Pause active icon, when paused, the Play active icon ▶ appears indicating that selecting it will start play whereupon the Pause active icon ‖ appears in lieu of the Play active icon ▶. Conversely, when playing, the Pause active icon ‖ appears indicating that selecting it will pause the play whereupon the Play active icon ▶ appears. The specific Protocol being run (i.e., played) is highlighted to indicate that it is active whereas previous Protocols that have already been run (i.e., played), are grayed-out to indicate that they have been run (i.e., played). The Next Protocol active icon ▶| immediately ceases running of the current Protocol and jumps forward to the next Protocol whereas the Previous Protocol active icon |◀ immediately ceases running of the current Protocol and jumps back to the previous Protocol. When a Pause is encountered during the sequential playing of the Protocols, playing is paused until the perfusionist manually reruns play by selecting the Play icon. It is noted that if the perfusionist has started flow via the Flow Knob, the Play/Pause active icon becomes inactive (i.e., is grayed-out).

Menu

The Menu active icon transitions to the Menu Screen (FIG. 9-1).

Arrest Agent

The Arr active icon transitions to the Arrest Agent Screen (see FIG. 15-24) which displays the concentration setting of the arrest agent in mEq/L within the range of 0 to 40 in increments of 1 (units may alternatively be set to mmol/L).

The volume gauge is displayed indicating the volume of fluid remaining in the Arrest pump chamber (25 bars/gauge; 2 cc/bar). The indicated level dynamically adjusts as fluid is being delivered. The display animates the delivery of the drug when the flow rate is greater than 0 and the arrest agent concentration is greater than 0 by simulating movement of the bar within the volume gauge.

The Arr active icon changes to "Arr Disabled" when the arrest agent pump is disabled. The current concentration values are saved (for restoring later) before setting the concentration values to 0 by messaging the MPS Console 14. Attempting to change the concentration of a disabled pump results in an alarm. If the perfusionist chooses to enable, the screen transitions automatically to the Arrest Agent Prime Screen. The time for the Arrest Agent Prime step is shows the approximate time remaining Once priming is complete the previously saved Arrest Agent concentration will be displayed and messaged to the MPS Pump.

The Arrest High Conc and Arrest Low Conc active icons select High or Low Arrest delivery modes. Either of these active icons is selectable but never both at the same time. The icon appropriately changes to indicate which selection is active. The selected Arrest delivery mode is saved in memory and messaged to the MPS Console 14.

The arrest concentration setting is grayed out and the simulated movement of the bar is suspended when VENT or RECIRC modes are activated.

Selecting the Arrest Label shows a tab labeled 'OFF?' if the pump is currently On, and 'ON?' if the pump is currently Off, simultaneously transitioning to the screen of FIG. 15-24. The tab is displayed for 3 seconds. If the tab is selected within the 3 seconds perform the action (described below) and then transition to Home. If the tab is not selected within 3 seconds, the tab fades away.

The Off status is conveyed by showing 'OFF' in the concentration value and graying out the display. The current concentration values are saved (for restoring later) before setting the concentration value to 0 and to message the MPS pump. The On status is conveyed by restoring the previously saved concentrations and to message the MPS pump.

The High Arrest Concentration active icon is used to set the High Arrest Delivery Concentration within a range of 0 to 40 in increments of 1 and to message the MPS Pump.

The Low Arrest Concentration active icon is used to set the Low Arrest Delivery Concentration with a range of 0 to 40 in increments of 1 and to message the MPS Pump. The Arrest Volume Remaining display shows the Remaining Arrest Volume in the Arrest chamber in 1 ml increments (not a settable parameter).

Separate alarms may be generated by the MPS Console 14 when the Arrest volume remaining drops below 10 mL and 0 mL. When the volume remaining reaches 10 ml, a volume countdown may be displayed in the message window with the volume gauge turning red. When the alarm is received, the arrest volume remaining, the High and Low Arrest concentrations are all forced to 0.

When the Arrest Refill active icon is selected it is renamed to "Done" and is flashed along with a flashing "Refill" in the volume remaining display. The Purge active icon is disabled and a notification message is displayed instructing the perfusionist to fill the arrest chamber (whereupon a message is sent to the MPS Console 14).

When the Done active icon is selected, or any valid key press or "flick", the Done active icon is changed to Refill and it stops flashing, the notification message is removed and the new arrest volume remaining is displayed (whereupon a message is sent to the MPS Console 14).

The Arrest Purge active icon is used to deliver a 1 ml bolus message to the MPS Pump. The text 'Purge' is displayed instead of the concentration to show that the purge operation is in progress. The Refill active icon and the Purge active icon become inactive during this process. Completion of the purge is determined by monitoring for a decrease in the Arrest Volume Remaining for a period of 3 seconds up to 12 seconds.

Selection of the SMArT active icon in FIG. 15-24 allows activation of the SMArT protocol described above. FIG.

15-24A illustrates the selection of the ECG active icon allowing activation of SMArT Hi or SMArT Lo active icons.

Additive

Referring to FIG. 15-25, selecting the Add active icon transitions to the Additive Mode screen which displays the Additive Concentration setting of the additive solution in ml/L. The range is 0 to 50 in increments of 1. The volume gauge is displayed indicating the volume of fluid remaining in the Additive chamber (25 bars/gauge; 2 cc/bar). The indicated level dynamically adjusts as fluid is being delivered. The display animates the delivery of the drug when the flow rate is greater than 0 and the additive concentration is greater than 0 by simulating movement of the bar within the volume gauge.

The display indicates when the additive pump is disabled whereupon the current concentration value is saved (for restoring later) before setting the concentration value to 0 and to message the MPS Console 14. Attempting to change the concentration of a disabled pump will result an alarm.

If the perfusionist chooses enable, the screen transitions automatically to the Additive Prime step (the time for the Additive Prime step is displayed only as the approximate time remaining) Once priming is complete the previously saved Additive concentration is displayed messaged to the MPS Pump.

The additive concentration setting is grayed out and the simulated movement of the bar is suspended when Vent Mode or Recirc Mode is activated.

Selecting the Additive Delivery Concentration highlights the parameter and displays the slider bar allowing it to be set within a range of 0 to 50 in 1 increments and messaged to the MPS Console 14. Selecting the Additive Label shows a tab labeled 'OFF?' if the pump is currently On, or 'ON?' if the pump is currently Off, simultaneously transitioning to Home. The tab is displayed for 3 seconds. If the tab is selected within the 3 seconds, the action is performed and then transitions to Home. If the tab is not selected within 3 seconds, the tab fades away.

The Off status is conveyed by showing 'OFF' in the concentration value and graying out the display. The current concentration value is saved (for restoring later) before setting the concentration value to 0 and to message the MPS Console 14. The On status is conveyed by restoring the previously saved concentration and to message the MPS Console 14.

The Additive Concentration active icon is used to set the Additive Delivery Concentration within a range of 0 to 50 in 1 increments and to message the MPS Console 14.

The Additive Conc is highlighted and ready to be set by default when this state is transitioned to. The Additive Volume remaining display shows the remaining Additive volume in the Additive chamber in 1 ml increments (not a settable parameter).

Separate alarms may be generated by the MPS Console 14 when the Additive volume remaining reaches 10 ml and 0 ml. When the volume remaining reaches 10 ml, a volume countdown is displayed in the message window and the volume gauge turns red. When the alarm is received, the volume remaining and the additive concentration are forced to 0.

When the Add Refill active icon is selected it is renamed to "Done" and is flashed along with a flashing "Refill" in the volume remaining display. The Purge active icon is disabled and a notification message is displayed instructing the perfusionist to fill the arrest chamber (whereupon a message is sent to the MPS Console 14).

When the Done active icon is pressed, or any valid key press or "flick", the Done active icon is changed to Refill and it stops flashing, the notification message is removed and the new arrest volume remaining is displayed (whereupon a message is sent to the MPS Console 14).

The Add Purge active icon is used to deliver a 1 ml bolus message to the MPS Pump. The text 'Purge' is displayed instead of the concentration to show that the purge operation is in progress. The Refill active icon and the Purge active icon become inactive during this process. Completion of the purge is determined by monitoring for a decrease in the Arrest Volume Remaining for a period of 3 seconds up to 12 seconds.

B:C Ratio

Referring to FIG. 15-26, the B:C active icon displays a volume gauge indicating the volume of fluid remaining in the Crystalloid bag (30 bars per gauge; 100 cc/bar). The indicated level dynamically adjusts anytime Crystalloid is being delivered. The display animates the delivery of crystalloid when the flow rate is greater than 0 by simulating movement of the bar within the volume gauge. When the ratio setting is set to 'blood' the volume gauge still shows remaining crystalloid volume, but is not animated since no crystalloid is being delivered.

The B:C Ratio shows the blood-to-crystalloid ratio. Selecting the B:C Ratio highlights the parameter and shows the slider bar. The B:C Ratio is settable within the following range of values:

| Blood | 66:1 | 49:1 | 39:1 | 32:1 | 27:1 | 24:1 | 21 - 2:1 | 1:1 | 1:2 - 9 | Cryst |
|---|---|---|---|---|---|---|---|---|---|---|

The changed value is saved in memory and messaged to the MPS Console 14.

As shown in FIGS. 15-26 through 15-29, selecting the B:C active icon transitions to the Blood-to-Crystalloid Ration Screen which allows the perfusionist to set the Blood-to-Crystalloid ratio within the previously defined range of values. The changed value is saved and messaged to the MPS Console 14. This is the parameter that is highlighted and ready to be set by default when this state is transitioned to.

The Percent (%) of crystalloid in the ratio mix is also displayed in the lower crystalloid ratios as shown in the table below.

| Ratio | 20:1 | 21:1 | 24:1 | 27:1 | 32:1 | 39:1 | 49:1 | 66:1 |
|---|---|---|---|---|---|---|---|---|
| Cryst (%) | 4.8 | 4.5 | 4.0 | 3.5 | 3.0 | 2.5 | 2.0 | 1.5 |

The Crystalloid Volume Remaining displays the volume of the crystalloid volume remaining When selected, the perfusionist may change the Crystalloid volume to any value between 0 and 3000 ml in 10 ml increments. The value is saved in memory and messaged to the MPS Console 14.

Selecting the Prime active icon when flow is zero transitions to Prime screen of FIG. 8G. When flow is >0 it is disabled. Selecting the Recirc active icon when flow is zero transitions to Recirc screen of FIG. 8I. When flow is >0 it is disabled.

Selecting the Flush active icon when flow is zero will Activate Vent mode, Activate Hold Vol mode, Change B:C ratio to blood, turn Add pump OFF, turn Arr pump OFF and set Flow Mode to Low Vol and then transition to Home.

Alarms may be generated when the Cryst volume remaining drops below 150 ml (alarm EC48), 50 ml (alarm EC49) and 0 ml (alarm EC50).

Temperature

Selection of H2O Temperature active icon transitions to the Temperature Screen (see FIG. 15-33). The Delivery Temperature display displays the delivery temperature within a range of 0 to 99° C. The Delivery Temperature value flashes when the displayed value is more than one degree different from the Warm temperature setpoint when in Warm Delivery Mode.

Selecting the Delivery Temperature value if the Temperature Delivery Mode is 'Warm' highlights the Warm Temp and show the slider bar to set the delivery temperature to a value between Off, 4° C. to 39° C. if in 39° C. Max Heat mode, or between Off, 4° C. to 42° C. if in 42° C. Max Heat Mode. A setting called 'Heaters Off' is a valid setting represented internally with a value of 0 and displayed as '- -'. The value is saved in memory and messaged to the MPS Console 14. If the Temperature Delivery Mode is 'Cold', the perfusionist will be instructed to change the temperature delivery mode to Warm before setting the Warm Delivery Temperature. The Water Temperature display displays the water temperature within a range of 0 to 99° C.

As shown in FIG. 15-30, the display presents the following circulation system conditions: circ system off, purging, purging stopped, heater diagnostics, heater disabled, and H2O and delivery temperature sensor disabled.

The Warm and Cold active icons select Warm or Cold temperature delivery Modes. These active icons are paired i.e. either one but never both are selectable at the same time. The icon appropriately changes to indicate which selection is active. The selected temperature delivery mode is saved in memory and messaged to the MPS Console 14.

The Warm Temperature setting is used to set the delivery temperature to a value between Off, 4° C. to 39° C. if in 39° C. Max Heat mode, or between Off, 4° C. to 42° C. if in 42° C. Max Heat Mode. This is the parameter that is highlighted and ready to be set by default when this state is transitioned to. The 'Heaters Off' setting is a valid setting conveyed to the perfusionist by displaying '--' and represented internally with a value of 0.

The Set Warm Temperature active icon is valid only if the Temperature Delivery Mode is 'Warm'. If the Temperature Delivery Mode is 'Cold' the perfusionist is instructed to change the temperature delivery mode to Warm before setting the Warm Delivery Temperature. The value shall be saved in memory and messaged to the MPS Console 14.

The H2O Circ active icon is used to turn the Circulation System ON or OFF. The value is saved in memory and messaged to the MPS Console 14.

The '39° C. Max' and '42° C. Max' active icons are used to set the Heat Mode's upper temperature range. The mode shall be saved in memory and messaged to the MPS Console 14.

The Continuous and Conserve Ice active icons are used to set the Cold Mode. The mode selection is saved in memory and messaged to the MPS Console 14.

The Purge active icon is used to purge the water circulation system and so messaged to the MPS Console 14 (allowed only if flow is zero).

A transparent clock icon flashes in the temperature display. The "H2O purge is in progress. About m:ss remaining" message with the timer counting down is shown in the message window. Any other message requiring use of the message window dismisses this message without the need to re-display.

The purge timer is an approximate timer and always starts at 30 seconds (and monitored to determine when the purge process is complete).

The Stop Purge active icon is used to stop the purge process whereupon the timer value is set to "--:--" and the graphical animation on the display and the countdown timer are frozen (and so messaged to the MPS Console 14). The Resume active icon is used to resume the stopped purge process whereupon the graphical animation and the timer are resumed (and messaged to the MPS Console 14).

ECG

Selecting the ECG active icon in Home Screens Chart View and Zoom View (FIGS. 14A & 14B) toggles between activating and deactivating the ECG. In all other active states selecting the ECG active icon transitions to the Home Screen ECG View (FIG. 14C). When activated, the ECG strip chart window (FIG. 15-34) is displayed in the Home Screen and the ECG active icon is highlighted.

Hold Volume

The Hold Vol active icon toggles between Activating and Canceling Hold Volume Mode. The icon is highlighted and shows the flashing Hold Vol tab to indicate that the Hold Volume mode is activated. The selected mode is saved in memory and messaged to the MPS Console 14. When activated the incremental volume counter stops counting and the Off timer immediately starts counting (even if flow >0). When Hold Vol is cancelled, the incremental volume counter resets and the On/Off timer operates normally. Every time flow is stopped with Hold Vol Mode activated, an audible beep is sounded.

Vent

The Vent active icon toggles between Activating and Canceling Vent Mode. It is active only when Flow is set to 0. The icon is highlighted and shows the flashing Vent tab to indicate that the Vent mode is activated. The selected Vent mode is saved in memory and messaged to the MPS Console 14. Every time flow is started with Vent Mode activated, an audible beep is sounded.

Graft

Selecting the Graft active icon shows a tab labeled 'OFF?' if Vein Graft mode is activated, or 'ON?' if not activated, and simultaneously transitions to the Graft Screen of FIG. 15-35. The tab remains displayed in this state (unlike in some other states where the tab fades after 3 seconds). If the tab is selected perform the action of activating or canceling Vein Graft mode it then transition to Home. When activated, the current Vein Graft upper and lower pressure limits are saved in memory and messaged to the MPS Console 14. The icon is highlighted and the Vein Graft tab is flashed to indicate that the Vein Graft mode is activated (in all states except when n Graft Screen). Every time flow is stopped with Vein Graft Mode activated, an audible beep is sounded. When Vein Graft Mode is cancelled, the current Antegrade and Retrograde upper and lower pressure limits are saved in memory and messaged to the MPS Console 14. Activating Vein Graft mode starts a new dose record. Cancelling Vein Graft mode ends the current dose record.

As shown in FIG. 15-36, the perfusionist is allowed to select from two different lists to label the Vein Graft—one selection from the Conduit list and one selection from either the Left or Right Graft list. If the Vein Graft has been labeled and Vein Graft mode has not been canceled since labeling, these labels are shown selected upon entering this screen. If not previously labeled, or if Vein Graft mode had been canceled, no labels are shown as being selected. Cancelling Vein Graft (selecting the G active icon and then selecting the 'OFF?' tab) resets all label selections. Only one selection (or no selection) is allowed in each list. Selecting a selected label deselects it.

When Confirm is selected, the label is remembered for use in the VG/Conduit column of the Dose History Table. When 'Confirm is selected with Vein Graft Mode activated, a new record entry is made in the Dose History Table. When 'Confirm is selected with Vein Graft Mode not activated, a new record entry is not be made immediately. The label selection is remembered and the new record is made the next time Vein Graft Mode is activated. Selecting the 'Pressure Limits' active icon transitions to the Vein Graft Pressure Screen of FIG. 15-6.

Regrograde/Antegrade

The Antegrade & Retrograde Delivery Direction active icons are visible to change the delivery direction. The Simulgrade Delivery direction can be selected from the Flow Mode Screen (FIG. 15-1). The delivery direction modes are mutually exclusive i.e. only one of these three modes can be activated at any given time. The current delivery direction setting is indicated by highlighting the active icon (or both active icons in the case of Simulgrade). The Delivery direction active icons are disabled when the Vent Mode is activated. Touching Retrograde when Retrograde is selected shall have no effect. Touching Antegrade when Antegrade is selected shall have no effect. Touching either Antegrade or Retrograde when Simulgrade is selected shall change the delivery direction setting.

The Home active icon transitions to one of the Home Screens (FIG. 13). When the Undo active icon is displayed, it replaces the Home active icon, and behaves like the Home active icon by confirming any changed value and transitioning to one of the Home Screens. The Stop Flow active icon displays when flow is greater than zero. When selected, the flow rate is set to 0 (messaged to the MPS Console 14). When the Stop active icon is selected, Hold Vol, Auto and Cyclic (but not Always Cyclic) modes are canceled the stop active icon is replaced with the Auto Flow active icon. The Auto Flow active icon (Stop active icon re-labeled) is displayed when flow is zero.

There are five possible target pressure sources: Ante External, Ante System, Retro External, Retro System and Vein Graft. If any of these sources are changed, the target pressure associated with the source becomes active. The Target Pressure value displayed within the Auto Flow active icon is updated.

When Auto Flow is selected, the Auto Target Pressure is messaged to the MPS Console 14 first and then Auto Mode may be activated by messaging the MPS Console 14. The Auto Flow active icon is disabled if either Vent or Recirc are activated. If the Auto Flow active icon is selected when Always Cyclic is active, normal flow mode is activated instead of cyclic flow mode for this one instance only.

Simulator Mode

The MCR Console may operate in a Simulator Mode only when it is disconnected from the main pump console and connected to a custom black box designed to put the MCR Console into simulator mode (it is not possible to enter or exit Simulator Mode at any other time). The simulator black box configures Channel A and B so one talks to the other, signaling the software to go into simulator/demo mode.

As shown in FIG. 16, in the Simulator Mode, the Home Screen is displayed along with the text 'DEMO MODE Not connected to console' along with an orange border along the bottom of the Home Screen. A Simulator Task runs in Simulator Mode and is responsible for receiving all messages that would usually be sent to the MPS Console 14 and for generating all the messages that the MCR Console is expecting from the MPS Console 14. No Dose Records, Protocols or Sequences are stored in memory.

The following table is a guideline for Priming in Simulator Mode.

| Prime Step | Simulated Duration (seconds) | Re-sync Time (seconds) | Simulated Flow (ml/min) | Simulated Pressure (mmHg) |
|---|---|---|---|---|
| Source Line Fill | 10 | 130 | 200 | 53 |
| Fluid Level Check | 7 | 100 | 200 | 61 |
| Air Expulsion | 5 | 95 | 200 | 58 |
| Blood Leak Test | 10 | 70 | 20 | 302 |
| Arrest Agent Prime | 5 | 50 | 0 | 218 |
| Additive Prime | 5 | 30 | 0 | 238 |
| Water Leak Test | 5 | 10 | 0 | 206 |

In Simulator Mode, the pressure readings are simulated 8 times per second using the guidelines shown in the table below. Variation in pressure readings my be random ±1% of the pressure value at a frequency varying randomly from 2 to 0.2 Hz. If the source pressure sensor is System for the active delivery mode, then make delivery pressure same as System pressure. Otherwise use the value shown in the table below. If the delivery pressure exceeds the upper pressure limit and Override is not active, set the delivery pressure at upper limit −5 mmHg and calculate a new flow rate using the inverse of the formula in the table below. The next time through the loop, since the upper limit is no longer violated, set the pressure and flow value as set by the perfusionist. This cycle will keep alternating creating the desired effect of bumping against the upper pressure limit setting.

| Delivery Mode | System Pressure (minimum 20 mmHg) | Delivery Pressure (minimum 10 mmHg) |
|---|---|---|
| Antegrade | Flow Rate/2 | Sys Press - 20 |
| Retrograde | Flow Rate/3 | Sys Press - 20 |
| Simulgrade | Flow Rate/3 | Sys Press - 20 |
| Vent | Flow Rate/1.5 | 23 |
| VG | Flow Rate/1.5 | Sys Press - 8 |

The following table may be used as a guideline for simulating temperatures.

| Circ Condition | Delivery Temperature | H2O Temperature |
|---|---|---|
| Warm, setpoint >28° C. | Setpoint | Setpoint +1° C. |
| Warm, setpoint <22° C. | Setpoint | Setpoint −1° C. |
| Warm, 22° C.-28° C. | Setpoint | Setpoint |
| Cold | 4° C. | 2° C. |

When transitioning from Warm to Cold or Cold to Warm, the temperature first jumps to 25° C. immediately. Then, the temperature may be increased or decreased (delivery and H2O) at the rate of 1° C. every 2 seconds. When Auto Mode is activated, the delivery pressure is remembered as the Target pressure. The delivery pressure is thereafter maintained at the target pressure and the flow is varied randomly ±10 ml/min in 1 ml/min increments at a frequency of once every 2 seconds. The target pressure increment and decrement active icons generate new Target pressure values which becomes the delivery pressure. When Auto Mode is activated, the target pressure is received followed by the Auto Enable message. This works exactly like Auto Mode as described earlier.

All volumes delivered may be calculated once per second based on Flow rate, ratio and concentration settings according to the table below. The flow rate determines the total Cardioplegia volume. The ratio setting is used to calculate the percentage of blood and crystalloid. The concentration setting is used to calculate the volume of Arrest and Additive delivered. All calculated volumes are returned in the Main Volume Status, Additive Volume Remaining and Arrest Volume Remaining messages once per second. Arrest and Additive Volume calculations are suspended in the Vent & Recirc modes. Scaling may be used for Arrest & Additive volumes because the incremental values calculated every second will be very small.

| Parameter | Formula | Message |
|---|---|---|
| totalCpdgVol | (FR/60) ml | MAIN_VOLUME_STATUS |
| BloodVol | (totalVol * blood)/ (blood + cryst) | MAIN_VOLUME_STATUS |
| CrystVol | totalVol − BloodVol | MAIN_VOLUME_STATUS |
| ArrestVol | ((totalVol * [ARR])/1000/ ASC) ml ASC is Arrest Source Conc (1 or 2 mEq/ mL) | ARREST_VOLUME_REMAINING |
| AddtiveVol | ((totalVol * [ADD])/1000) ml | ADDITIVE_VOLUME_REMAINING |

When the Arrest & Additive refill process is initiated, refill occurs to 35 mL by sending the Initial Additive Volume or Initial Arrest Volume message after a 5 second delay. When the Purge process is initiated, 1 mL is delivered by sending the above 2 messages after a 2 second delay. When the On time reaches 30 seconds while flowing in Simulgrade mode, 'Occlusion' alarm (223) is generated. The alarm screen overwrites the "Demo mode" text at the bottom of the screen.

Flash Loader Utility

If the MCR is powered up with the REED SWITCH signal activated, it enters the Flash Loader Utility Mode and displays the Flash Loader Screen of FIGS. 17-1 through 17-5. Touching any area in the MCR, PCS or PMS targets shifts focus to that target by graying out the other two targets. When Test is touched, a 'R U Alive' message is sent and up to 2 seconds is awaited to receive the response one target at a time. If a response is received the Passed status is shown in green. If not, the Failed status is shown in red. Select Files and Start are grayed out during the Test process.

When Select Files is touched, the navigation window is shown listing all compatible files (only files of compatible format are displayed) available on the connected USB storage media. If the USB storage is not inserted or no compatible files are available, a blank window is displayed. When a file is touched, it is added to the top of the list of the appropriate target. When a selected file in the target window is touched, the file is removed from the list. The selection window is removed when either a target window is touched or the close active icon is closed. For the MCR Console, only one file of each file type is allowed (i.e., only one .img or .app file). If a .img file is already in the selected file window, selecting another file with the same extension .img is disallowed by sounding the invalid key alarm tone. On the PCS & PMS target windows, multiple selections of the same file type .crc are allowed.

When Start is touched, start programming all the selected files while showing the progress in each target window. The file being flashed is shown in yellow. All active icons are grayed out.

The Flash Loader communicates with the PCS & PMS targets via the RS-485 Channel B serial interface. The User is notified via the Aborted status if an upload is unsuccessful (other target may proceed uninterrupted). When all files are transmitted the Complete Status is displayed. The MCR target performs a verification of the copied file and the Utility displays the complete or aborted status.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A console for controlling the delivery of cardioplegia to a patient, comprising in combination:
    a computer for computer-controlled perfusion of cardioplegia into the patient according to parameters, at least some of said parameters including a set of protocols, said computer then sequencing said protocols in a specific order fora particular patient and to deliver cardioplegia to the patient in accordance with said protocols in said sequence,
    an integrated display/touch screen for displaying cardioplegia information and information about the patient and allowing inputting of parameters, said protocols and said sequence via the display/touch screen into the console for computer-controlled perfusion of cardioplegia into the patient in accordance with said protocols in said sequence;
    a flow knob allowing manual control the cardioplegia flow rate, said manual control via said flow knob taking precedence over any in-process computer-controlled cardioplegia perfusion into the patient by suspending any in-process perfusion of cardioplegia into the patient in accordance with said protocols in said sequence, whereby manual control of the cardioplegia perfusion into the patient resumes, and
    an interface cable including an interface operatively connected between the console and a cardioplegia pump.

2. The console as set forth in claim 1, wherein the pump provides electrical power to the console via said interface cable such that the console powered on when the pump is powered on.

3. The console as set forth in claim 1, further including an electrocardiogram input allowing an electrocardiogram waveform to be displayed on the display/touch screen.

4. The console as set forth in claim 1, further including one or more of a an interface port to export or import data to or from an external storage media, a printer port for network or local printing, a communication port for connectivity communications.

5. The console as set forth in claim 1, further including a switch input for a switch that boots the console into a flash loader mode.

6. The console as set forth in claim 5, wherein said switch comprises a reed switch concealed within a housing of the console, said reed switch including contacts that are closed when a magnet is moved in close proximity to said reed switch.

7. The console as set forth in claim 1, wherein said display/touch screen comprises a graphical user interface.

8. The console as set forth in claim 7, wherein said display/touch screen displays a Select Step allowing selection of a Case Manager Step, a New Case Setup Step, a Resume Case Step or a Menu Step.

9. The console as set forth in claim 8, wherein said Case Manager Step allows setup of said protocols and said sequence in said specific order.

10. The console as set forth in claim 8, wherein said New Case Setup Step allows setup for a new patient based upon one or more of User Defaults, a Previous Case, an Existing Protocol or Existing Sequence.

11. The console as set forth in claim 8, wherein said New Case Setup Screen includes one or more of User Defaults, An Existing Protocol, Previous Case Parameters and An Existing Sequence active icons corresponding to the User Defaults Step, Previous Case Step, Existing Protocol Step and Existing Sequence Step.

12. The console as set forth in claim 11, wherein selection of said User Default active icon displays Review/Modify Parameter screens, which is scrolled through to display the factory-predefined user default parameters.

13. The console as set forth in claim 12, wherein the Review/Modify Parameter screens includes a Prime active icon corresponding to the Prime Step allowing transfer to the Prime Step in preparation for delivering cardioplegia to the patient.

14. The console as set forth in claim 7, wherein said display/touch screen displays a Prime Step that when selected primes the pump to begin perfusion.

15. The console as set forth in claim 7, wherein said display/touch screen displays a Home Screen Step that when selected allows monitoring the computer-controlled delivery of cardioplegia to the patient.

16. The console as set forth in claim 15, wherein said Home Screen Step allows manual pause or stopping of the delivery of cardioplegia to the patient in which case a Resume Case Step then allows subsequent resumption of delivery of cardioplegia to the patient.

17. The console as set forth in claim 15, wherein said Home Screen Step allows return to a Case Manager Step to temporarily change previously-setup protocol or sequencing parameters.

18. The console as set forth in claim 7, wherein, while either in the Select Screen Step or while in the Home Screen Step, a Menu Screen Step is selected to perform various administrative functions.

19. The console as set forth in claim 7, wherein said display/touch screen displays active or passive icons for appropriate controls and parameters relevant to a step being performed, the active icons representing such controls and parameters being selectable as desired for manipulation of the parameters or navigation to previous or succeeding screens.

20. The console as set forth in claim 7, wherein at the conclusion of delivery of cardioplegia to the patient, the parameters used are stored in memory as the Previous Case Parameters.

21. The console as set forth in claim 20, wherein selection of the Previous Case Parameters displays the previous-case parameters in the Review/Modify Parameter screens review or modification, and when completed, transfers to the Prime Step in preparation for delivering cardioplegia to the patient.

22. The console as set forth in claim 7, further including predefining a collection of parameters, labeling them and storing in memory as Existing Protocols for later use via Case Manager.

23. The console as set forth in claim 22, wherein in lieu of using User Default or Previous Case parameters respectively corresponding to the User Default Step or Previous Case Step, an Existing Protocol may be selected in the New Case Setup screen corresponding to the Existing Protocol Step, whereupon a listing of the predefined Existing Protocols is displayed.

24. The console as set forth in claim 23, wherein upon selection of one of the Existing Protocols, its predefined parameters are displayed the Review/Modify Parameter screens for review or modification, and when completed, transfer to the Prime Step.

25. The console as set forth in claim 24, further including sequencing a series of Existing Protocols to be used in sequence, labeling and storage in memory as Sequences for later use via Case Manager.

26. The console as set forth in claim 25, wherein upon selection of one of the Existing Sequences listed in the New Case Setup screen, the selected Existing Sequence's sequence of Protocols are displayed for review or modification and when completed, transferred to the Prime Step.

27. The console as set forth in claim 26, further including a play icon for initiating the Sequence.

28. The console as set forth in claim 27, further including pause and stop icon to pause or stop the running of the Sequence.

29. The console as set forth in claim 28, further including a skip icon for skipping one or more of the Protocols of the Sequence.

30. The console as set forth in claim 7, further including a data viewer.

31. The console as set forth in claim 7, further including a training simulator.

32. The console as set forth in claim 7, further including vein graft labeling.

33. The console as set forth in claim 7, further including displaying the volume of cardioplegia to be delivered.

34. The console as set forth in claim 33, further including displaying either the total of the volume of cardioplegia to be delivered or the additional volume of cardioplegia to be delivered.

* * * * *